United States Patent
Mauldin et al.

(10) Patent No.: US 11,373,303 B2
(45) Date of Patent: *Jun. 28, 2022

(54) SYSTEMS AND METHODS FOR ULTRASOUND IMAGING

(71) Applicant: Rivanna Medical LLC, Charlottesville, VA (US)

(72) Inventors: Frank William Mauldin, Charlottesville, VA (US); Kevin Owen, Crozet, VA (US)

(73) Assignee: Rivanna Medical, Inc., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,372

(22) Filed: May 3, 2020

(65) Prior Publication Data

US 2020/0273169 A1 Aug. 27, 2020

Related U.S. Application Data

(63) Continuation of application No. 16/008,743, filed on Jun. 14, 2018, now Pat. No. 10,679,347, which is a (Continued)

(51) Int. Cl.
*G06T 7/00* (2017.01)
*A61B 8/08* (2006.01)
(Continued)

(52) U.S. Cl.
CPC .......... *G06T 7/0012* (2013.01); *A61B 8/0858* (2013.01); *A61B 8/0875* (2013.01);
(Continued)

(58) Field of Classification Search
CPC ......... G06T 5/009; G06T 7/0012; G06T 7/30; G06T 11/60; G06T 15/08; G06T 2200/04;
(Continued)

(56) References Cited

U.S. PATENT DOCUMENTS

| 5,970,499 A | * | 10/1999 | Smith | ...................... G06F 16/30 |
| | | | | 707/999.102 |
| 7,570,791 B2 | * | 8/2009 | Frank | ................... A61B 6/4441 |
| | | | | 382/128 |

(Continued)

OTHER PUBLICATIONS

Penney et al. "Validation of a two-to three-dimensional registration algorithm for aligning preoperative CT images and intraoperative fluoroscopy images." Medical physics 28.6 (2001): 1024-1032. (Year: 2001).*

*Primary Examiner* — Katrina R Fujita
(74) *Attorney, Agent, or Firm* — Woods Rogers PLC; Nathan A. Evans

(57) ABSTRACT

In some embodiments, a method comprises: obtaining a 2D ultrasound image of an imaged region of a subject, the imaged region comprising bone; identifying model template cross-sections of a 3D model of the bone corresponding to the 2D image at least in part by registering the 2D ultrasound image to the 3D model, wherein the model template cross-sections are defined prior to obtaining such 2D image, the model template cross-sections having size and shape representative of a population of potential subjects; identifying at least one location of at least one landmark feature of the bone in the 2D image based on results of the registration; and generating a visualization that includes: a visualization of the 2D image and a visualization of one of the identified cross-sections of the 3D model, wherein the visualization indicates the at least one location of the at least one landmark feature.

14 Claims, 10 Drawing Sheets

Related U.S. Application Data continuation of application No. 14/770,893, filed as application No. PCT/US2014/018732 on Feb. 26, 2014, now Pat. No. 10,134,125.

(60) Provisional application No. 61/770,437, filed on Feb. 28, 2013.

(51) Int. Cl.

| | |
|---|---|
| *G06T 5/00* | (2006.01) |
| *G06T 7/30* | (2017.01) |
| *G06V 10/42* | (2022.01) |
| *G06V 10/60* | (2022.01) |
| *A61B 8/00* | (2006.01) |
| *G06T 11/60* | (2006.01) |
| *G06T 15/08* | (2011.01) |
| *G06V 10/46* | (2022.01) |

(52) U.S. Cl.
CPC ............ *A61B 8/461* (2013.01); *A61B 8/5223* (2013.01); *A61B 8/5246* (2013.01); *A61B 8/5269* (2013.01); *G06T 5/009* (2013.01); *G06T 7/30* (2017.01); *G06T 11/60* (2013.01); *G06T 15/08* (2013.01); *G06V 10/42* (2022.01); *G06V 10/60* (2022.01); *G06T 2200/04* (2013.01); *G06T 2207/10132* (2013.01); *G06T 2207/30008* (2013.01); *G06V 10/467* (2022.01)

(58) Field of Classification Search
CPC . G06T 2207/10132; G06T 2207/30008; A61B 8/0858; A61B 8/0875; A61B 8/461; A61B 8/5223; A61B 8/5246; A61B 8/5269; G06V 10/42; G06V 10/467; G06V 10/60
See application file for complete search history.

(56) References Cited

U.S. PATENT DOCUMENTS

| | | | | |
|---|---|---|---|---|
| 2004/0017935 | A1* | 1/2004 | Avinash | G06T 7/38 382/131 |
| 2005/0271302 | A1* | 12/2005 | Khamene | G06T 15/005 382/294 |
| 2008/0118125 | A1* | 5/2008 | Mahesh | G06T 7/32 382/128 |
| 2009/0274350 | A1* | 11/2009 | Pavlovskaia | G06K 9/00 382/128 |
| 2010/0128953 | A1* | 5/2010 | Ostrovsky-Berman | G06T 7/344 382/131 |
| 2014/0235998 | A1* | 8/2014 | Kim | A61B 8/5261 600/424 |
| 2016/0143627 | A1* | 5/2016 | Vignon | A61B 8/466 600/437 |

* cited by examiner

SYSTEMS AND METHODS FOR ULTRASOUND IMAGING

RELATED APPLICATIONS

This application is a continuation of and claims priority to U.S. patent application Ser. No. 16/008,743, filed on Jun. 14, 2018 entitled "SYSTEMS AND METHODS FOR ULTRASOUND IMAGING," which claims priority to, and is related to, U.S. patent application Ser. No. 14/770,893, filed on Aug. 27, 2015, entitled "SYSTEMS AND METHODS FOR ULTRASOUND IMAGING," which claims priority to, is related to, and is a U.S. national application based on International Application No. PCT/US2014/018732, filed on Feb. 26, 2014, now International Publication No. WO 2014/134188 A1, entitled "SYSTEMS AND METHODS FOR ULTRASOUND IMAGING," which claims the benefit of and priority to U.S. Provisional Application No. 61/770,437, filed on Feb. 28, 2013, entitled "MODEL REGISTRATION-BASED IMAGING TECHNIQUES AND ASSOCIATED SYSTEMS AND DEVICES," each of which are incorporated by reference herein in its entirety.

STATEMENT OF FEDERALLY SPONSORED RESEARCH

This invention was made with government support under award number R43EB015232 awarded by the National Institute of Biomedical Imaging and Bioengineering of the National Institutes of Health and award number 1214788 awarded by the National Science Foundation. The government has certain rights in the invention.

TECHNICAL FIELD

Aspects of the technology described herein relate to ultrasound imaging and related systems and methods. Some aspects relate to generating ultrasound images of bone in a subject being imaged. Some aspects relate to visualizing ultrasound images of bone in a subject being imaged.

BACKGROUND

Medical ultrasound may be used as an alternative to X-ray for bone imaging. However, conventional ultrasound systems are limited in their application. For example, in many conventional ultrasound systems, artifacts may be generated from off-axis reflections, which make the produced image less useful to the user. In addition, many conventional systems produce difficult-to-interpret two-dimensional (2D) images. Although certain transducer geometries may be used to reduce artifacts and three-dimensional (3D) ultrasound images of bone may be obtained, such images nonetheless generally suffer from low sensitivity, as the ultrasound signal strength is highly dependent on the angle of the bone surface with respect to the acoustic beam axis. Therefore, while the error of reconstructed bone surfaces may be very low, the low specificity and sensitivity of the reconstruction may still yield an image that is challenging to interpret. Additionally, the production of freehand images in 3D remains challenging due to, for example, cumulative motion estimation bias distortions. For at least these reasons, ultrasound images generated by conventional ultrasound imaging techniques may be difficult to interpret.

SUMMARY

Some embodiments are directed to a method of processing ultrasound data. The method comprises using at least one computer hardware processor to perform obtaining ultrasound data generated based, at least in part, on one or more ultrasound signals from an imaged region of a subject; calculating shadow intensity data corresponding to the ultrasound data; generating, based at least in part on the shadow intensity data and at least one bone separation parameter, an indication of bone presence in the imaged region; generating, based at least in part on the shadow intensity data and at least one tissue separation parameter different from the at least one bone separation parameter, an indication of tissue presence in the imaged region; and generating an ultrasound image of the subject at least in part by combining the indication of bone presence and the indication of tissue presence.

Some embodiments are directed to a system for processing ultrasound data. The system comprises at least one computer hardware processor configured to perform obtaining ultrasound data generated based, at least in part, on one or more ultrasound signals from an imaged region of a subject; calculating shadow intensity data corresponding to the ultrasound data; generating, based at least in part on the shadow intensity data and at least one bone separation parameter, an indication of bone presence in the imaged region, generating, based at least in part on the shadow intensity data and at least one tissue separation parameter different from the at least one bone separation parameter, an indication of tissue presence in the imaged region; and generating an ultrasound image of the subject at least in part by combining the indication of bone presence and the indication of tissue presence.

Some embodiments are directed to at least one non-transitory computer-readable storage medium storing processor executable instructions that, when executed by at least one computer hardware processor, cause the at least one computer hardware processor to perform a method of processing ultrasound data. The method comprises obtaining ultrasound data generated based, at least in part, on one or more ultrasound signals from an imaged region of a subject; calculating shadow intensity data corresponding to the ultrasound data; generating, based at least in part on the shadow intensity data and at least one bone separation parameter, an indication of bone presence in the imaged region; generating, based at least in part on the shadow intensity data and at least one tissue separation parameter different from the at least one bone separation parameter, an indication of tissue presence in the imaged region; and generating an ultrasound image of the subject at least in part by combining the indication of bone presence and the indication of tissue presence.

In some embodiments, the ultrasound data comprises a plurality of ultrasound data values each corresponding to a respective voxel in a plurality of voxels, and wherein calculating the shadow intensity data comprises calculating a shadow intensity value for a first of the plurality of voxels at least in part by calculating a weighted sum of ultrasound data values corresponding to voxels in the plurality of voxels that are located at least a threshold number of voxels away from the first voxel.

In some embodiments, including any of the preceding embodiments, the threshold number of voxels is greater than or equal to an axial resolution of an imaging system used to generate the ultrasound data.

In some embodiments, including any of the preceding embodiments, the ultrasound data comprises a plurality of ultrasound data values each corresponding to a respective voxel in a plurality of voxels, and wherein generating the indication of bone presence in the imaged region comprises calculating, for a first of the plurality of voxels, a bone intensity value based at least in part on a ratio of a first ultrasound data value corresponding to the first voxel and a first shadow intensity value corresponding to the first voxel.

In some embodiments, including any of the preceding embodiments, calculating the bone intensity value is performed at least in part by applying a weighting function to the ratio of the first ultrasound data value and the first shadow intensity value, wherein the weighting function is parameterized by the at least one bone separation parameter.

In some embodiments, including any of the preceding embodiments, the at least one bone separation parameter is calculated based, at least in part, on the shadow intensity data.

In some embodiments, including any of the preceding embodiments, the ultrasound data comprises a plurality of ultrasound data values each corresponding to a respective voxel in a plurality of voxels, and wherein generating the indication of tissue presence in the imaged region comprises calculating, for a first of the plurality of voxels, a tissue intensity value based at least in part on a first shadow intensity value corresponding to the first voxel.

In some embodiments, including any of the preceding embodiments, calculating the tissue intensity value is performed at least in part by evaluating a weighting function at least in part by using the first shadow intensity value, wherein the weighting function is parameterized by the at least one tissue separation parameter.

In some embodiments, including any of the preceding embodiments, the weighting function is a sigmoidal weighting function.

In some embodiments, including any of the preceding embodiments, the at least one tissue separation parameter is calculated based, at least in part, on the shadow intensity data.

In some embodiments, including any of the preceding embodiments, combining the indication of bone presence and the indication of tissue presence is performed based, at least in part, on a desired bone-to-tissue contrast and/or a desired contrast-to-noise ratio.

Some embodiments are directed to a method for visualizing ultrasound data. The method comprises using at least one hardware processor to perform obtaining a two-dimensional (2D) ultrasound image of an imaged region of a subject, the imaged region comprising bone; identifying a cross-section of a three-dimensional (3D) model of the bone corresponding to the 2D ultrasound image at least in part by registering the 2D ultrasound image to a three-dimensional (3D) model; identifying at least one location of at least one landmark feature of the bone in the 2D ultrasound image based on results of the registration; and generating a visualization of the 2D ultrasound image and the identified cross-section of the 3D model of the bone, wherein the visualization indicates the at least one location of the at least one landmark feature.

Some embodiments are directed to a system for visualizing ultrasound data. The system comprises at least one computer hardware processor configured to perform obtaining a two-dimensional (2D) ultrasound image of an imaged region of a subject, the imaged region comprising bone; identifying a cross-section of a three-dimensional (3D) model of the bone corresponding to the 2D ultrasound image at least in part by registering the 2D ultrasound image to a three-dimensional (3D) model; identifying at least one location of at least one landmark feature of the bone in the 2D ultrasound image based on results of the registration; and generating a visualization of the 2D ultrasound image and the identified cross-section of the 3D model of the bone, wherein the visualization indicates the at least one location of the at least one landmark feature.

Some embodiments are directed to at least one non-transitory computer-readable storage medium storing processor executable instructions that, when executed by at least one computer hardware processor, cause the at least one computer hardware processor to perform a method of visualizing ultrasound data. The method comprises obtaining a two-dimensional (2D) ultrasound image of an imaged region of a subject, the imaged region comprising bone identifying a cross-section of a three-dimensional (3D) model of the bone corresponding to the 2D ultrasound image at least in part by registering the 2D ultrasound image to a three-dimensional (3D) model; identifying at least one location of at least one landmark feature of the bone in the 2D ultrasound image based on results of the registration; and generating a visualization of the 2D ultrasound image and the identified cross-section of the 3D model of the bone, wherein the visualization indicates the at least one location of the at least one landmark feature.

In some embodiments, generating the visualization comprises overlaying the identified cross-section on the 2D ultrasound image.

In some embodiments, including any of the preceding embodiments, the overlaying comprises performing an affine transformation of the identified cross-section of the 3D model.

In some embodiments, including any of the preceding embodiments, the overlaying comprises overlaying the identified cross-section on the 2D ultrasound image with a degree of transparency, the degree of transparency determined using a measure of quality of fit between the 2D ultrasound image and the identified cross-section.

In some embodiments, including any of the preceding embodiments, generating the visualization further comprises generating the visualization to include at least a portion of the 3D model of the bone and information identifying how the 2D ultrasound image corresponds to the 3D model of the bone.

In some embodiments, including any of the preceding embodiments, the imaged region of the subject includes at least a portion of the subject's spine and the 3D model of the bone comprises a 3D model of at least the portion of a spine.

In some embodiments, including any of the preceding embodiments, the at least one landmark feature of the bone comprises a spinous process of a lumbar spine and/or an interlaminar space of a lumbar spine.

In some embodiments, including any of the preceding embodiments, the registering is performed at least in part by using information about motion of the subject during generation of the 2D ultrasound image.

Some embodiments, including any of the preceding embodiments, further comprise displaying the generated visualization.

BRIEF DESCRIPTION OF THE DRAWINGS

Various aspects and embodiments of the technology will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
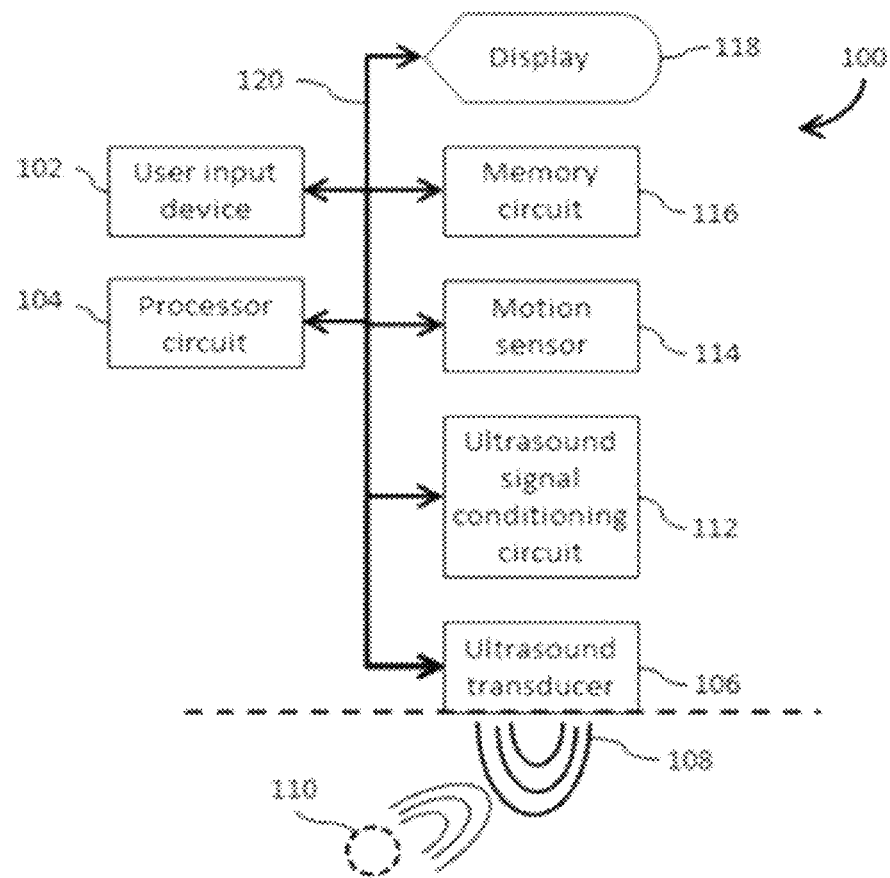
FIG. 1 is a block diagram of an exemplary apparatus that may include at least one ultrasound transducer and at least one processor configured to perform model-based bone imaging, the output of which may be rendered to the apparatus display, in accordance with some embodiments of the disclosure provided herein.

The inventors have recognized that, when imaging an area of a subject that includes bone and tissue, identifying regions of bone and tissue presence may help to generate improved ultrasound images of the imaged area that may be easier to interpret. The regions of bone and tissue presence may each be identified by taking into account ultrasound shadow caused by bone presence in the imaged area. Accordingly, in some embodiments, an ultrasound image of a subject may be generated by: (1) obtaining ultrasound data generated based on ultrasound signals from an imaged region of the subject; (2) generating shadow intensity data corresponding to the ultrasound data; (3) generating indications of bone and tissue presence based on the generated shadow intensity data; and (4) combining the indications of bone and tissue presence. In this way, ultrasound images having a desired bone-to-tissue contrast and/or a desired contrast-to-noise ratio may be obtained, and such images may be easier to interpret.

The inventors have also recognized that an ultrasound image comprising bone may be easier to interpret if presented (e.g., to a user) with reference to an anatomical model of the bone being imaged. Accordingly, some embodiments relate to visualizing ultrasound data by generating a visualization of a two-dimensional (2D) ultrasound image that includes a corresponding portion of a three-dimensional (3D) bone model. The corresponding portion of the 3D model (e.g., a 2D cross-section) may be identified at least in part by using a registration technique to register the 2D ultrasound image to the 3D model. The registration results may be used to identify the location(s) of one or more anatomical landmarks in the 2D ultrasound image and the generated visualization of the image may indicate one or more of the identified locations.

Aspects of the technology described herein are explained in the context of spinal anesthesia guidance, but it should be appreciated that the technology described herein is useful for and may be applied in other settings. For example, the technology described herein may be used for other clinical applications where ultrasound is used to image bone such as, but not limited to, guiding of orthopedic joint injections, performing lumbar punctures, or performing diagnosis of bone fractures.

In some embodiments, a method for performing ultrasound imaging is provided. The method may comprise enhancing bone contrast by using the reciprocal of a shadow intensity value at every pixel location in an ultrasound image, where the shadow intensity value may be defined as:

$$S(i, j) = \sum_{k=i+\alpha}^{M} w_{k,i} I(k, j)$$

wherein S(i,j) is the shadow intensity output, I(i,j) is the envelope detected ultrasound image data, $w_{k,i}$ is a depth weighting, and a is an offset.

In some embodiments, the method comprises registering at least one 2D ultrasound image to a 3D model of a region comprising bone; and producing a 2D and/or 3D visualization of the region comprising bone wherein the visualization is derived, at least in part, from the registration of the at least one 2D ultrasound image to the 3D model of the spine.

The aspects and embodiments described above, as well as additional aspects and embodiments, are described further below. These aspects and/or embodiments may be used individually, all together, or in any combination of two or more, as the technology described herein is not limited in this respect.

FIG. 1 illustrates an example of an apparatus 100 that may be used for generating and/or displaying ultrasound images. As shown, apparatus 100 comprises at least one processor circuit 104, at least one ultrasound transducer 106, at least one ultrasound signal conditioning circuit 112, at least one motion sensor 114, at least one memory circuit 116, and display 118. The one or more ultrasound transducers 106 may be configured to generate ultrasonic energy 108 to be directed at a target tissue structure 110 within a subject being imaged (e.g., the ultrasound transducers 106 may be configured to insonify one or more regions of interest within the subject). Some of the ultrasonic energy 108 may be reflected by the target tissue structure 110, and at least some of the reflected ultrasonic energy may be received by the ultrasound transducers 106. In some embodiments, the at least one ultrasonic transducer 106 may form a portion of an ultrasonic transducer array, which may be placed in contact with a surface (e.g., skin) of a subject being imaged.

In some embodiments, ultrasonic energy reflected by the subject being imaged may be received by ultrasonic transducer(s) 106 and/or by one or more other ultrasonic transducers, such as one or more ultrasonic transducers part of a linear transducer array. The ultrasonic transducer(s) that receive the reflected ultrasonic energy may be geometrically arranged in any suitable way (e.g., as an annular array, a piston array, a linear array, a two-dimensional array) or in any other suitable way, as aspects of the disclosure provided herein are not limited in this respect. As illustrated in FIG. 1, ultrasonic transducer(s) 106 may be coupled to the ultrasonic signal conditioning circuit 112, which is shown as being coupled to circuits in apparatus 100 via bus 120. The ultrasonic signal conditioning circuit 112 may include various types of circuitry for use in connection with ultrasound imaging such as beam-forming circuitry, for example. As other examples, the ultrasonic signal conditioning circuit may comprise circuitry configured to amplify, phase-shift, time-gate, filter, and/or otherwise condition received ultrasonic information (e.g., echo information), such as provided to the processor circuit 104.

In some embodiments, the receive path from each transducer element part of a transducer array, such as an array including the first ultrasonic transducer 106, may include one or more of a low noise amplifier, a main-stage amplifier, a band-pass filter, a low-pass filter, and an analog-to-digital converter. In some embodiments, one or more signal conditioning steps may be performed digitally, for example by using the processor circuit 104.

In some embodiments, the apparatus 100 may be configured to obtain ultrasonic echo information corresponding to one or more planes perpendicular to the surface of an array of ultrasound transducers (e.g., to provide "B-mode" imaging information). For example, the apparatus 100 may be configured to obtain information corresponding to one or more planes parallel to the surface of an array of ultrasound transducers (e.g., to provide a "C-mode" ultrasound image of loci in a plane parallel to the surface of the transducer array at a specified depth within the tissue of the subject). In an example where more than one plane is collected, a three-dimensional set of ultrasonic echo information may be collected.

In some embodiments, the processor circuit 104 may be coupled to one or more non-transitory computer-readable media, such as the memory circuit 116, a disk, or one or more other memory technology or storage devices. In some embodiments, a combination of one or more of the first ultrasonic transducer 106, the signal conditioning circuit 112, the processor circuit 104, the memory circuit 116, a display 118, or a user input device 102 may be included as a portion of an ultrasound imaging apparatus. The ultrasound imaging apparatus may include one or more ultrasound transducers 106 configured to obtain depth information via reflections of ultrasonic energy from an echogenic target tissue structure 110, which may be a bone target.

In an example, the processor circuit 104 (or one or more other processor circuits) may be communicatively coupled (e.g., via bus 120) to one or more of a user input device 102 and the display 118. For example, the user input device 102 may include one or more of a keypad, a keyboard (e.g., located near or on a portion of ultrasound scanning assembly, or included as a portion of a workstation configured to present or manipulate ultrasound imaging information), a mouse, a touch-screen control, a rotary control (e.g., a knob or rotary encoder), a soft-key touchscreen aligned with a portion of the display 118, and/or one or more other controls of any suitable type.

In some embodiments, the processor circuit 104 may be configured to perform model registration-based imaging and presenting the constructed image or images to the user via the display 118. For example, a simultaneous 2D/3D display may be presented to the user via the display 118, as described in further examples below.

In some embodiments, ultrasonic energy reflected from target tissue 110 may be obtained or sampled after signal conditioning through the ultrasound signal conditional circuit 112 as the apparatus 100 is swept or moved across a range of locations along the subject surface (e.g., skin). A composite may be constructed such as using information about the location of at least the transducer 106 of apparatus 100 (or the entire apparatus), such as provided by the motion sensor 114, and information about reflected ultrasonic energy obtained by the ultrasonic transducer 106. Motion sensor 114 may be any suitable type of sensor configured to obtain information about motion of the subject being imaged (e.g., position information, velocity information, acceleration information, pose information, etc.). For example, the motion sensor 114 may comprise one or more accelerometers configured to sense acceleration along one or more axes. As another example, the motion sensor 114 may comprise one or more optical sensors. The motion sensor 114 may be configured to use one or more other techniques to sense relative motion and/or absolute position of the apparatus 100, such as using electromagnetic, magnetic, optical, or acoustic techniques, or a gyroscope, independently of the received ultrasound imaging information (e.g., without requiring motion tracking based on the position of imaged objects determined according to received ultrasonic information). Information from the motion sensor 114 and ultrasonic energy obtained by the ultrasonic transducer 104 may be sent to the processor circuit 104 via bus 120. The processor circuit 104 may be configured to determine motion or positional information of at least the transducer of apparatus 100 using processes described in further examples below. The motion or positional information may be used to carry out model registration-based imaging.

Other techniques may include using one or more transducers that may be mechanically scanned, such as to provide imaging information similar to the information provided by a two-dimensional array, but without requiring the user to manually reposition the apparatus 100 during a medical procedure. The apparatus 100 may be small and portable, such that a user (e.g., a physician or nurse) may easily transport it throughout healthcare facilities or it may be a traditional cart-based ultrasound apparatus.

In some embodiments, apparatus 100 may provide imaging using non-ionizing energy, as it may be safe, portable, low cost, and may provide an apparatus or technique to align a location or insertion angle of a probe to reach a desired target depth or anatomical location. Examples of the model registration-based process described below are focused on spinal anesthesia clinical procedures whereby a healthcare professional inserts a probe in or around the spinal bone anatomy to deliver anesthetics. In this instance the model registration-based process uses a 3D model of the spinal bone anatomy. However, the apparatus and methods described herein are not limited to being used for imaging of the spine and may be used to image any suitable bone or bones. In addition, apparatus 100 may be employed in clinical diagnostic or interventional procedures such as orthopedic joint injections, lumbar punctures, bone fracture diagnosis, and/or guidance of orthopedic surgery.

It should be appreciated that the apparatus 100 described with reference to FIG. 1 is an illustrative and non-limiting example of an apparatus configured to perform ultrasound imaging in accordance with embodiments of the disclosure provided herein. Many variations of apparatus 100 are possible. For example, in some embodiments, an ultrasound imaging apparatus may comprise one or more transducers for generating ultrasonic energy and circuitry to receive and process energy reflected by a target being imaged to generate one or more ultrasound images of the subject, but may not comprise a display to display the images. Instead, in some embodiments, an ultrasound imaging apparatus may be configured to generate one or more ultrasound images and may be coupled to one or more external displays to present the generated ultrasound images to one or more users.

Figure 2:
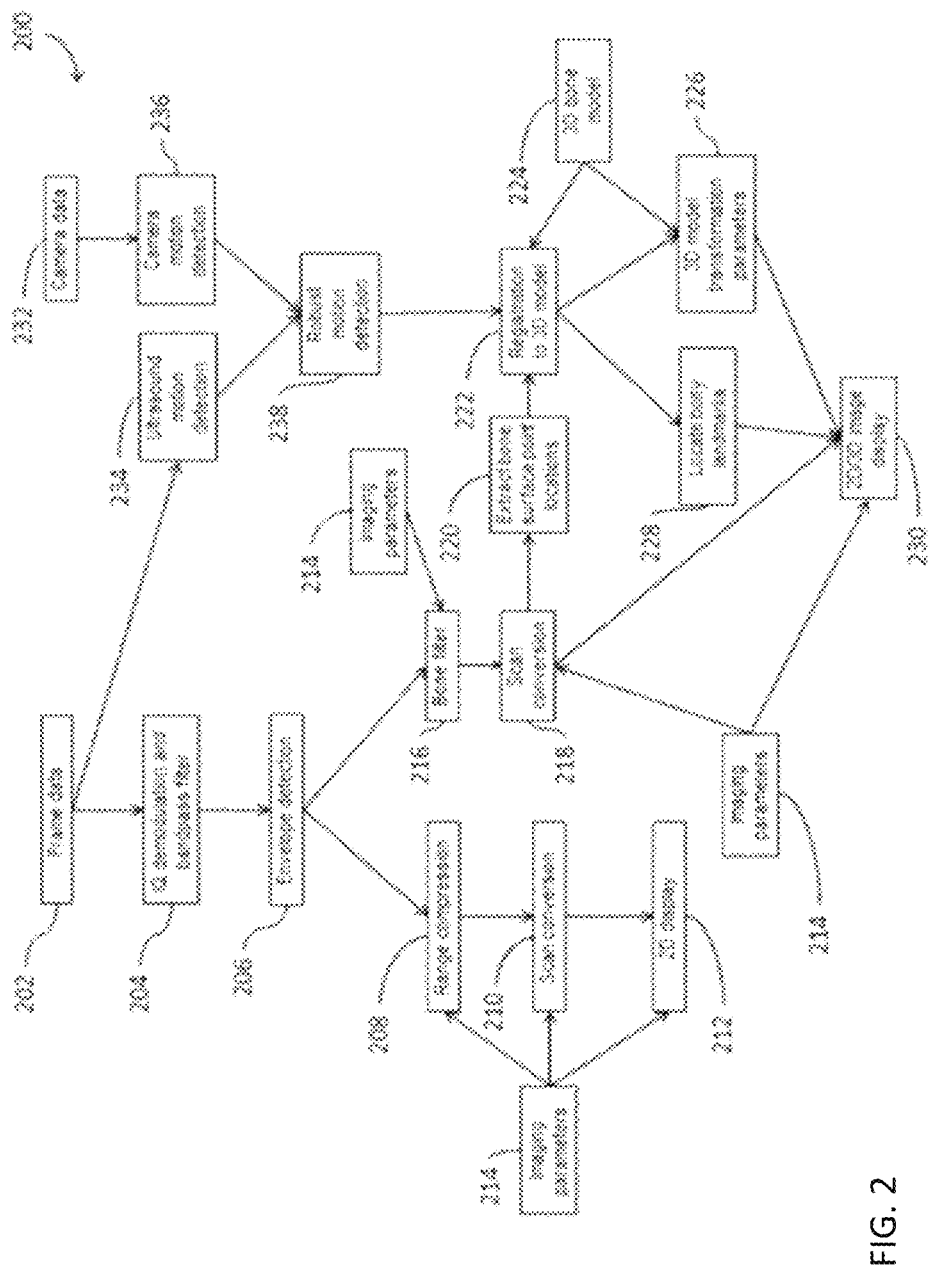
FIG. 2 is a block diagram of an exemplary procedure by which model-based bone imaging may be performed, in accordance with some embodiments of the disclosure provided herein.

FIG. 2 is a block diagram of an illustrative process 200 for ultrasound imaging, in accordance with some embodiments of the disclosure provided herein. Process 200 may be performed by any suitable system or apparatus such as a portable apparatus (e.g., apparatus 100 described with reference to FIG. 1) or a fixed apparatus.

One branch of process 200 begins at act 202, when ultrasound frame data is received. The ultrasound frame data may be ultrasound echo data (e.g., radio frequency or 'RF' signal data), which has been sent to a processor circuit 104 after conditioning with an ultrasound signal conditioning circuit 112. The ultrasound frame data received at act 202 may be conditioned at acts 204-210 prior to being used to generate a 2D image. As illustrated in FIG. 2, the ultrasound frame data may be demodulated into a complex baseband signal (IQ demodulation) and band pass filtered at act 204. Subsequently, envelope detection may be performed at act 206. Subsequently, range compression may be performed at act 208 and scan conversion may be performed at act 210. Range compression 208 may be performed using a logarithm mapping function or any other suitable function to increase the dynamic range of the image. Scan conversion 210 may be performed when ultrasound frame data is in non-rectilinear coordinates, such as polar coordinates. Some of the above-discussed acts are described in more detail below.

In some embodiments, a bone filter may be applied to ultrasound frame data after the frame data has been demodulated, band pass filtered, and envelope detection has been performed. This is shown by the arrow from act 206 to act 216. The bone filter may operate on ultrasound frame data after envelope detection (real baseband signal) is performed at act 206. This remaining branch of the block diagram relates to the inventive model registration-based imaging approach. In some embodiments, a "fitting" or registration act may be performed between a 3D bone model 224, such as a lumbar spine model, and the ultrasound 2D image or compilation of ultrasound 2D images after extracting certain bone surface point locations 220. Finally, in one embodiment, robust motion detection 238 may support accurate fitting or registration.

In some embodiments, frame data 202 may be obtained from one or more ultrasound sensors (e.g., a linear array of ultrasound sensors, a two-dimensional array of ultrasound sensors, one or more piston ultrasound transducers, etc.). The ultrasound sensor(s) may be configured to convert detected acoustic ultrasound energy into a received electronic "echo trace" that is digitally sampled (e.g., by using analog to digital converters), which is a component of the ultrasound signal conditioning circuit 112. Various analog or digital filtering may be performed before the digitally sampled frame data is transferred to a microprocessor unit. The frame data may comprise A-lines obtained from different spatial locations along the scan plane. In the linear array for instance, this may be achieved by electronically translating the transmit and/or receive apertures along the array. In the piston transducer, this may be achieved by mechanically sweeping the transducer about an arc and collecting A-lines at different positions along the arc.

Bandpass filtering and IQ demodulation may be performed at act 204 using one or more quadrature filters or in any other suitable way. Quadrature filters may be two separate filters that are 90 degrees out of phase from one another but otherwise having the same bandwidth. The bandwidth and number of samples, or "taps", for the set of filters may be chosen based on the desired center frequency and roll-off. Filtering may be performed by convolving each filter, an in phase (I) and quadrature (Q) filter, by each of the A-lines. The output may be twice the size of the original frame data and may comprise I and Q components derived from the convolution of the I and Q quadrature filters. Other methods to IQ demodulate a radio-frequency signal include multiplication by two versions of a sinusoidal carrier signal 90 degrees out of phase with each other (I and Q), followed by low-pass filtering to remove one of the modulation images, leaving only the I and Q baseband signal components.

In some embodiments, performing envelope detection (e.g., at act 206) may comprise computing the magnitude of each I and Q sample combination, treated as a complex number, (I real, Q imaginary). For example if $I(i,j)$ and $Q(i,j)$ are the sample values from the ith row and jth column of the I or Q components, respectively, then the envelope-detected output is computed as the magnitude of the two values:

$$\sqrt{I(i,j)^2 + Q(i,j)^2}.$$

At act 208, range compression may be performed on the envelope detected signal data. Range compression may comprise computing a logarithm (e.g., base 10) of the ultrasound data or square root or some other similar mapping function that may increase the dynamic range of the 2D display image pixel data sent to the apparatus display 118 via a bus 120. The mapping function may be adjusted depending on the imaging parameters 214, such as gain or contrast. For instance, the mapping function $M(P(i,j))$ that maps pixel $P(i,j)$ to a range compressed output value may include an offset that has the effect of changing gain, for example shifting $P(i,j)$ values higher or lower: $M(P(i,j)+t)$. For $t>0$, gain is increased thereby providing for an overall higher amplitude image.

At act 210, scan conversion 210 may be performed to convert range-compressed data from a non-Cartesian coordinate system (e.g., a polar coordinate system) to a Cartesian coordinate system. In embodiments where the ultrasound data is obtained (e.g., sampled) in the Cartesian coordinate system, as the case may be with linear array-based imaging, then scan conversion 210 may not be needed.

At act 212, the ranged compressed (and optionally scan-converted) data may be used to generate an image for display to a user. For example, if process 200 were performed by using apparatus 100, act 212 may be performed at least in part by transferring data from the apparatus processor circuit 104 to the apparatus user display 118 via bus 120.

In some embodiments, imaging parameters 214 may be set by the user by way of the apparatus user input device 102 and may include, for example, zoom, depth, gain, image contrast, or bone-to-tissue contrast. Though, in other embodiments, one or more of the imaging parameters 214 may be set automatically. In some embodiments, the image parameters may affect the output of the bone filter 216, scan conversion 218, or simultaneous 2D/3D image display. For example, in some embodiments, the bone filter 216 may be computed only over the depth range set by the imaging parameters and therefore reduce the amount of computational resources used and/or the time needed to perform the computations.

In ultrasound imaging, bone surfaces may be characterized as brightly reflecting interfaces followed by an (ultrasound) "shadow." The term ultrasound shadow refers to the substantial absence of a reflected ultrasound signal from one or more imaged areas because of the presence of one or more objects (e.g., a bone) that reflect(s) at least some (e.g., all) of the ultrasound energy passing through the object(s). A shadow generally occurs when imaging a bone surface because the ultrasound waves do not pass through the bone surface and are instead mostly reflected at the bone surface.

Accordingly, in some embodiments, a priori knowledge of bone surface reflections may be used to enhance bone surfaces in an ultrasound image while at least partially attenuating other soft tissue regions in the ultrasound image. Such enhancement and/or attenuation may be performed at least in part by using a bone-filtering step (e.g., step 216 described herein). An image obtained by using a bone-filtering step may possess an enhanced delineation of bone structures as compared to the unfiltered image. The bone filter computes, in some embodiments, a "shadow intensity" value for each of one or more (e.g., every) pixel in the envelope detected frame data (e.g., as computed at act 206 of illustrative process 200). The shadow intensity may be computed as a weighted sum of image intensity values at all image depths greater than the current pixel value with a range offset. Therefore, bone surface locations, which exhibit substantial shadowing, may exhibit a low shadow intensity value while regions of soft tissue will exhibit a relatively higher shadow intensity value. In some embodiments, the bone-filtered image may be obtained by multiplying each of one or more pixels in the envelope detected frame data by the reciprocal of each pixel's respective shadow intensity value. One or more additional functions may be used to combine the shadow intensity information with the image intensity values (e.g., envelope-detected frame data) with the goal of producing a desired image output that possesses enhanced bone-to-tissue contrast or contrast-to-noise ratio (CNR) when compared with the original, unfiltered frame data.

Scan conversion 218 may be performed on the output of the bone filtering, for example, in the same manner as described with respect to scan conversion 210 performed on the range compressed 208 image data.

In one embodiment, the output of the bone filtering performed at act 216 may be scan converted, at act 218, and displayed to a user (e.g., via a display such as display 118). In another embodiment, a model registration-based approach may be configured to yield a display with both the 2D bone filter output along with information indicative of the registration output including the position and scale of the model target tissue after registration to the image data. An initial step to register the scan converted bone filtered image to a 3D bone model 224 may be performed based at least in part on bone surface point locations extracted, at act 220, from the scan converted bone filtered output obtained at act 218. Bone surface points may be extracted automatically. For example, in some embodiments, bone surface points may be extracted by setting an image intensity threshold such that values in the scan converted bone filtered output 218 above a threshold are automatically identified as possible bone surface locations to be used to perform the registration of the possible bone surface locations to the 3D model at act 222. In another example, an algorithm may first locate groups of consecutive pixels along A-lines with intensities greater than a threshold value. This threshold value may be adaptively set as a multiple of the mean value from the bone filter output 216. Within each grouping of pixels, a single point may be extracted to more efficiently represent that segment of bone. This single point can, for example, correspond to the point location with the maximum bone filter output value or maximum shadow intensity. The extracted point locations and their bone filter output values or shadow intensities may then be accumulated into a vector for registration with the 3D bone model 224.

In some embodiments, the act 222 of registration to a 3D model may comprise performing point set registration, which may comprise identifying a translation and/or scaling of one of two sets of point data that minimizes a cost function or "similarity metric." An example cost function involves Euclidean distance and image intensity of the "best match". In embodiments where a point set registration method is applied, a first set of points may be extracted from both bone filtered frame data (e.g., the extracted bone surface point locations obtained at act 220 of process 200) and a second set of points may be extracted from the 3D bone model 224. In the 3D bone model 224, the point set may be easily accessed if the 3D bone model is formatted in a computer aided design (CAD) file type such as an .stl file. The vertices from the .stl list may be used as the point set. Frame-to-frame displacement information and previous registration outputs, e.g. model position, scaling, and rotation, may be used to inform the 3D model registration 222. For example, if zero displacement between frames is detected, then the previous registration solution is highly likely compared to registration solutions with greatly varied translation, scaling, or rotation. Therefore, the translation and scaling solutions corresponding to the previous registration solution may be assigned a higher weighting.

It should be appreciated that other methods besides point set registration may be used to perform the registration at act 222 of process 200. As one illustrative example, template matching may be used, whereby registration is performed directly between the 3D model and the scan converted bone filtered image 218. In such an embodiment, the act of extracting bone surface point locations may be omitted. Different metrics may be used to find the optimal registration output. For example, the maximum image intensity summed along the intersections of the 3D model and the image may be found for different translations (the x, y, and z dimensional shifts of the 2D image along the 3D volume) and scaling (the multiplication of the pixel size dimension relative to the 3D model inter-element spacing where an element is a point or surface comprising the 3D volume). The correct registration would correspond to a translation and scaling combination that results in the maximum summed intensity.

Another illustrative non-limiting example of a registration technique that may be performed at act 222 of process 200 is a coarse-to-fine registration technique. A coarse-to-fine registration technique may take as inputs the extracted bone surface locations from one or more scan converted bone filtered image frames and the 3D bone model 224. The point set obtained from the 3D bone model may be translated along a spatial grid relative to the set of points extracted from the bone filtered image frame(s) 220. The 3D bone model may be allowed to scale or rotate about a similar parameter grid with a grid spacing and grid extent. At each positional, scaling, and rotation combination along the grid, a quantity from a cost function may be calculated. The initial grid extent and interval spacing may be larger in the coarse registration phase compared with fine registration. An example cost function used in a preferred embodiment is the following:

$$\text{cost} = \sum_{i=1}^{N} \min_{j \in [1,M]} \left( \frac{dist(\text{template}(i), \text{bone}(j))}{\text{intensity}(\text{bone}(j))} \right) \quad (1)$$

where N is the total number of points in the 3D bone model, M is the total number of points extracted from the bone filtered image frame, 'dist' is a distance calculation between the model point 'i' and the bone filtered image point 'j', and 'intensity' is the bone filtered or shadow intensity value of the pixel containing the corresponding extracted bone surface point 'j'. The cost value represents a minimum value by associating, for each template point, a bone surface point that minimizes a distance to bone surface intensity ratio. The coarse registration positional, scaling, and rotational solution is chosen as the combination along the parameter grid that produces the lowest registration score using the cost function, such as the cost function of Equation (1). Finally, the fine registration may be performed. The purpose of the fine registration is to produce a more accurate measure of the registration output. The accuracy of the coarse registration may be limited due to forced positional, scaling, and rotational grid sampling. The fine registration starts with the coarse registration solution and allows for much more fine sampling but over a smaller parameter grid extent, which is centered about the coarse registration resolution. Alternatively, a fine registration process may include individually registering control points in the 3D bone model to points in the extracted bone point set from the bone filtered image frame 220 using the same cost function in Equation (1). Control points are typically chosen as landmark points along the model geometry, such as spinous process, lamina, or vertebral body.

The inventors have recognized the clinical benefits of automatically locating certain bony landmarks for the ultrasound apparatus user. In this way, the user is not required to interpret the 2D B-mode or scan converted bone-filtered image. Instead the model registration-based approach may identify and locate certain anatomy for the user. The registration output 222, such as a point set registration, is a set of translation, scaling, or rotational parameters. The location of bony landmarks, such as spinal bone landmarks, may be read from the 3D model after applying the prescribed translation, scaling, and rotation. In the application of imaging a lumbar spine, for example, the landmarks may include the spinous process and interlaminar space. These landmark depth locations may be useful to present to the user as they may help to inform the depth of a needle insertion attempt, such as in a neuraxial anesthesia procedure. The 2D/3D image display 230 may present information indicative of the location of these landmarks to the user on the apparatus user display 118 as will be described in further exemplary embodiments below.

Figure 3:
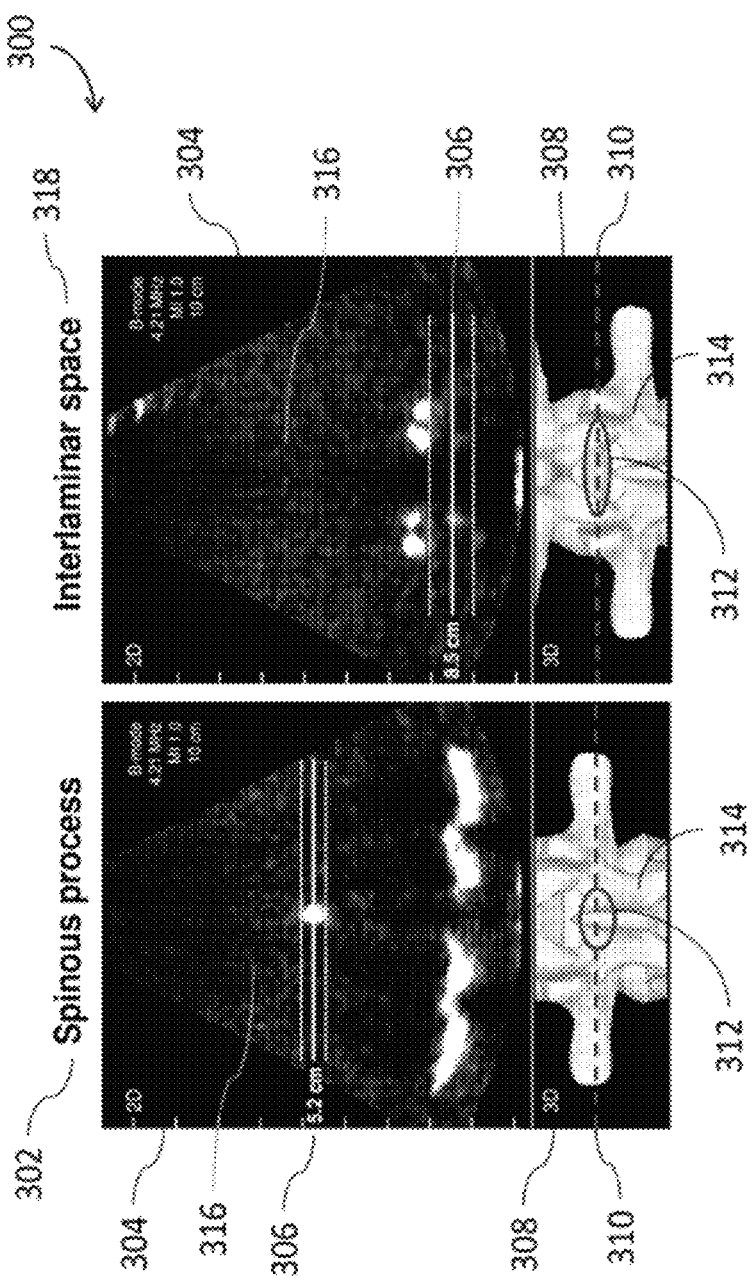
FIG. 3 illustrates a visualization of a 2D ultrasound image of an imaged area together with a 3D model of at least a portion of the imaged area, in accordance with some embodiments of the disclosure provided herein.

Additionally, the translation, scaling, and rotational parameters, termed the 3D model transformation parameters 226, may be applied to the 3D bone model representation 224 for the purpose of displaying the transformed 3D model to the user display screen 118. These model transformation parameters 226 are also useful for a 2D image display where a portion of the 3D model is shown as an overlay to a 2D image. The overlay may represent the intersection of the 2D image plane and the 3D registered bone model. For example, FIGS. 2-3 illustrate a 2D cross-sectional overlay in a 2D image region of the display.

In the application of ultrasound-guided spinal anesthesia, a 3D lumbar spine bone model is suggested as the 3D bone model 224. The model may be a computer aided design (CAD) model. It may be of various file formats including .stl and .dicom. The model may be obtained from computed tomography (CT) or from manual graphics rendering. A set of models may be used if desirable where the model yielding the greatest cost function minimization, such as lowest Euclidean distance, is used for the display. Other bone structures may be used as the 3D bone model, such as femur, knee, or hip. A 3D point-set bone model representation may be captured with the use of as few as two separate 2D cross-sections. In a preferred embodiment applied to 3D spinal bone models, transverse cross-section "model template" vectors may be used. Each model template may represent key landmark anatomy such as the spinous process or vertebral body landmark anatomy. Templates may be defined prior to imaging with the goal of having a size and shape representative of the human population. The 3D point-set spine representation may be more finely sampled, with many model templates, with the trade-off of increased computational time.

Output of the model registration-based process may be displayed to a user at act 230. In some embodiments, the output may comprise a 2D image of a subject being imaged and/or a 3D image of a corresponding 3D bone model.

As one illustrative non-limiting example, a user may be presented with a 2D ultrasound image derived from a range compressed and scan converted 2D image frame 212 or a bone filtered and scan converted image frame 218; a 3D representation of the bone model after transformation based on the registration 3D model transformation parameters 226; landmark locations 228 automatically identified and highlighted in any suitable way (e.g., by using color, transparency, shading, overlaid indicators, etc.); indicators in the 3D display that show the location of the current 2D ultrasound scan plane relative to the 3D bone model registration output; and indicators to indicate a "goodness-of-fit" or uncertainty relative to the registration process. For example, the uncertainty value may be based on the minimized cost function output associated with the registration solution, such as in Equation (1). This information displayed to the user is superior as compared to a conventional 3D rendering, which does not utilize automatic landmark localization or registration, because it may provide a more intuitive display with measurement of interest automated. For example, the model 3D image may be noiseless and exhibit perfect sensitivity to bone detection. The landmarks do not necessarily require manual selection and translation measurements, as they may be automatically located for display on the apparatus user display 118. Overall, the approach allows the user to visualize both 2D and 3D images and the 2D location with respect to the 3D volume.

The inventors have also recognized that motion or positional sensing may be used to improve the robustness and accuracy of the model registration-based process. In an exemplary embodiment, image data may be obtained, for example, from a motion sensor such as camera 232. For example, a series of image frames from a CMOS cell-phone class camera sensor may be captured at successive time intervals. Camera motion detection 236 may be performed using a motion detection algorithm that examines two or more camera image frames and uses differences between the frames to estimate relative motion between the camera and what the camera is imaging. Any of numerous types of motion estimation algorithms may be used including, but not limited to, 2D normalized cross-correlation and 2D sum-absolute-difference. The output of camera motion detection may form an estimate of relative camera motion, in 2 or more dimensions, in addition to a measure of estimate quality, for example estimated standard deviation of one or more measurement components.

An ultrasound motion detection 234 algorithm examines two or more ultrasound image frames and uses differences between the frames to estimate relative motion between the ultrasound transducer and the target. Relative motion may be estimated using any of numerous types of motion estimation algorithms may be used including, but not limited to, 2D normalized cross-correlation and 2D sum-absolute-difference. For motion out of the scan plane, the statistical decorrelation properties of ultrasound speckle may be used, with optional training data, to form a motion estimate. Still other techniques may be used. The output of ultrasound motion detection is an estimate of relative ultrasound transducer/tissue motion in up to 3 dimensions, along with a measure of estimate quality, for example estimated standard deviation of one or more measurement components.

The motion estimates from camera motion detection 236 and ultrasound motion detection 234 may be combined to form robust motion detection 238. The two input motion estimates may be combined using estimate quality values, (e.g. standard deviation or similar statistical quality measure). One form of estimate combination is to assume that both input estimates are independent, normally distributed variables, and to sum values from both sources, weighted by the inverse of the individual standard deviations, forming a maximum likelihood combined estimate. However, other methods of combining two individual estimates could be used, as aspects of the disclosure provided herein are not limited in this respect. In each case, the combined motion estimate should have, on average, less error than each individual estimate.

Further specifications and exemplary embodiments related to the bone filter 216 will now be recited. In some embodiments, the bone filter first computes shadow intensity values for one or more (e.g., every) locations in the frame data. A shadow intensity may be calculated as a weighted sum of all image intensity values at the same scan line but at all depths greater than the current depth plus an offset, α:

$$S(i, j) = \sum_{k=i+\alpha}^{M} w_{k,i} I(k, j) \qquad (2)$$

where S(i,j) is the shadow intensity output, I(i,j) is the envelope detected ultrasound image data, and $w_{k,i}$ is a depth weighting, which varies with k and i. The indices i range from 1 through the M number of depth samples in I. The index j ranges from 1 through the N number of scan lines. The weighting values $w_{k,i}$ are typically constant with k and chosen as a function only of i such that the output S(i,j) corresponds to the average envelope detected values in column j from i+α through M. However, in other embodiments the weightings may be variable such as to be more or less sensitive to pixel locations further or closer to the current pixel location k, j. In some embodiments, the offset a is determined as the thickness in the range, or depth, dimension of a bone surface in the envelope detected ultrasound data. In this way, if pixel depth location i corresponds to a bone surface point, then the shadow intensity output sums only over regions of signal dropout (i.e. shadow) rather than incorporating signal from bone. That is to say, if pixel depth location i were located at the leading, most shallow, edge of a bone surface, then pixel locations i through i+(α−1) are comprised of signal from the bone surface while i+α through M locations are comprised of shadow only. The exact value of a may be determined by experimental observation or derived from the axial resolution of the imaging system.

The output of the bone filter may then be calculated as the pointwise division of the envelope detected ultrasound image with the shadow intensity values with an additional factor, T, which is chosen as a small number in order to avoid division by 0.

$$B(i,j)=I(i,j)/(S(i,j)+\tau) \qquad (3)$$

Figure 5:
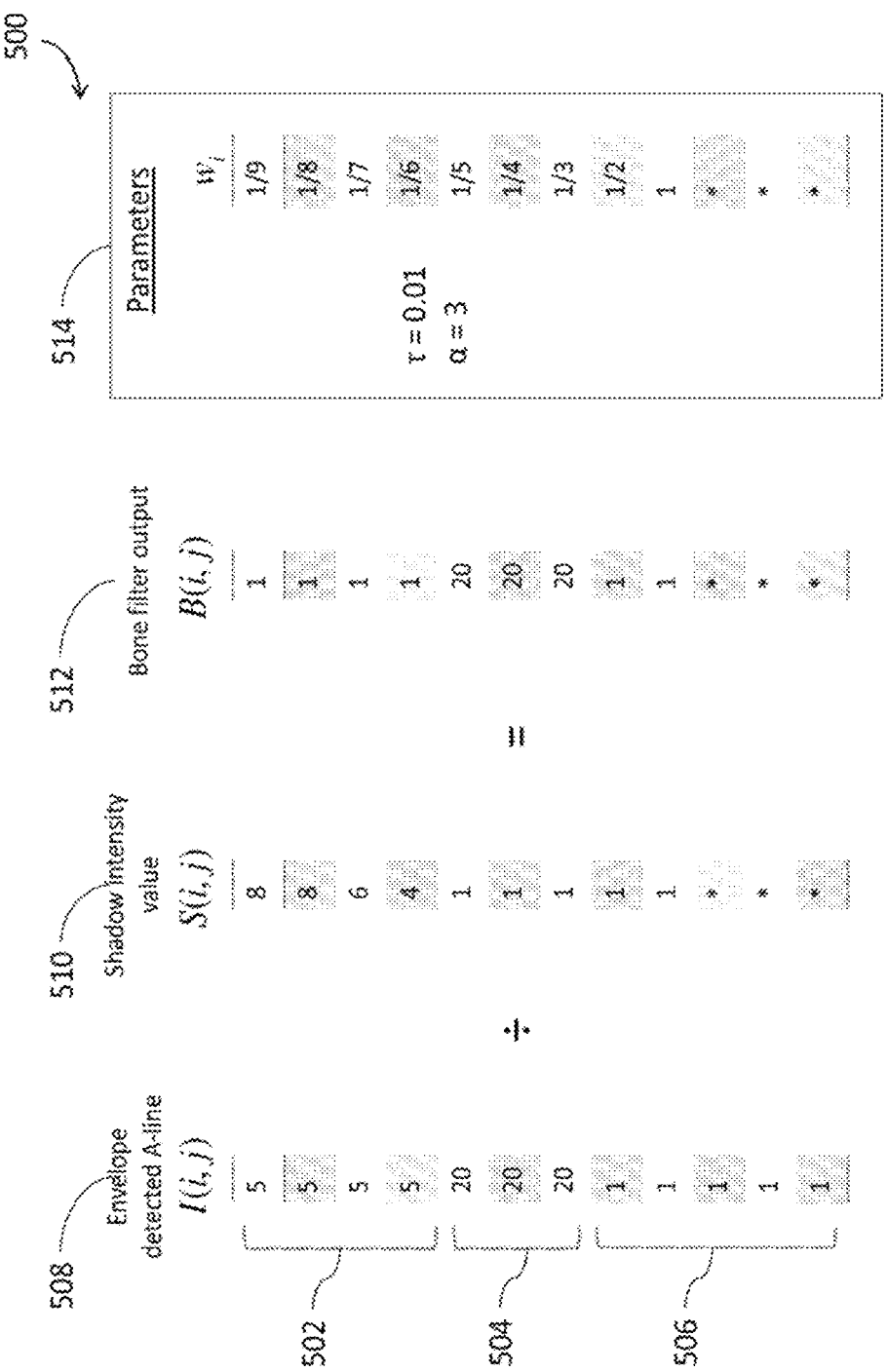
FIG. 5 is a diagram illustrating the calculation of a bone filter, in accordance with some embodiments of the disclosure provided herein.

It should be appreciated that the bone filter output may be formed using a function other than a pointwise-division as described with respect to Equation 3. For example, a sigmoidal function may be used. An exemplary embodiment is illustrated in FIG. 5. The column of envelope detected A-line data 508 is illustrated for each entry i where the values mimic the typical pattern of tissue (medium intensity) 502, then typical values for bone surface (high intensity) 504, then typical values for acoustic shadow (intensity dropout) 506. The value of j, in this set of embodiments, is constant due to only one A-line being illustrated. The column of corresponding shadow intensity values 510 shows the shadow intensity values that result from the example envelope detected A-line values 508 using filter parameters 514 and Equation 2. As illustrated by the filter parameters 514, an a value of 3 is used as it corresponds to the thickness of the bone region 504. The value of τ=0.01, is a small number relative to I(i,j) values and avoids division by 0. Values of the bone filter output 512 are rounded to the nearest whole number. Values of the depth weighting function $w_{k,i}$ are illustrated in the parameters 514 and only vary with i and are constant with k. The values are chosen such that shadow intensity outputs are an average across the i+α through M summation. The bone filter output 512 in this exemplary embodiment is the element-wise product of the envelope detected A-lines values 508 with the reciprocal of shadow intensity values 510, again rounded to the nearest whole number. As illustrated in FIG. 5, the output of the bone filter 512 exhibits an improved contrast between bone regions 504 and tissue regions 502 (20:1 versus 20:5). Entries with the asterisk correspond to locations where a shadow intensity value cannot be computed because i+α>M. In an exemplary embodiment, these entries would be filled with zeros or some other number.

Figure 6:
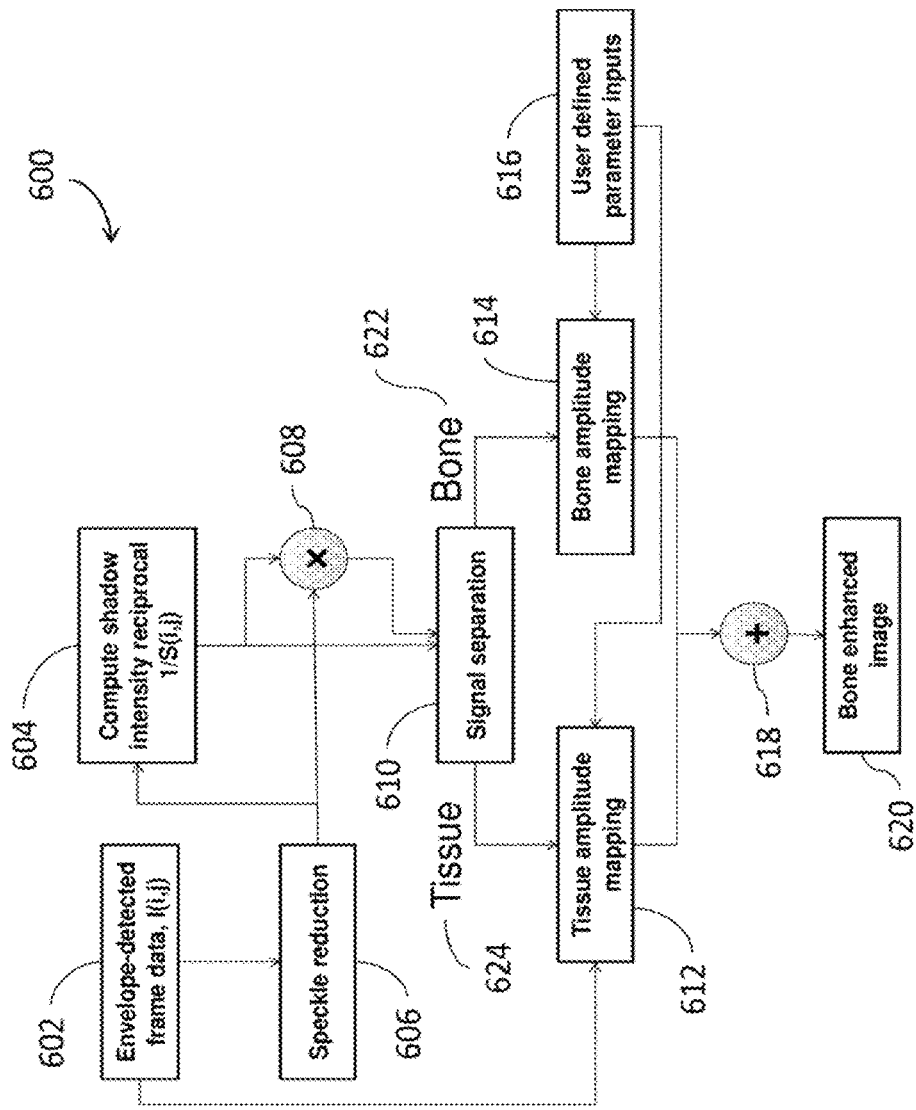
FIG. 6 is a flowchart of an illustrative process of forming a bone-enhanced image, in accordance with some embodiments of the disclosure provided herein.

Another exemplary embodiment of a procedure in which bone or bone deformation along a bone surface is detected, enhanced, or identified from the received ultrasound energy is illustrated in the block diagram FIG. 6. This exemplary procedure is based on computation of a shadow intensity value and a bone filter output described, such as described in Equation 3, as a basis for separating bone and tissue components. With bone and tissue regions segmented, the final "bone enhanced" image 620 may be reconstructed with arbitrary contrast or contrast-to-noise or some other similar image quality metric that may be user defined. In this embodiment the "bone enhanced" image 620 may be displayed to the device display 118 in addition, or as a substitution, to the bone filter output 216 described by Equation 3. The exemplary embodiment of a bone filter described in FIG. 6 takes as an input envelope-detected frame data, I(i,j) 602, such as generated from the FIG. 2 embodiment at the output of the envelope detection 206 step. A speckle reduction 606 preprocessing step may be performed to improve performance of the ultimate signal separation 610 into a tissue component 624 and bone component 622. The speckle reduction steps may comprise, in one embodiment, a combined approach of wavelet transform thresholding and bilateral filtering. In one embodiment, the discrete wavelet transform may be computed using Daubechies wavelets (or any other suitable wavelets) and thresholding may be performed on coefficients in the lateral high, combination high, and axial high frequency sub-images. After zeroing wavelet coefficients below a threshold in each sub-image, the inverse discrete wavelet transform may be applied, and finally, bilateral filtering. In another embodiment, bilateral filtering alone may be used to reduce image speckle.

The reciprocal of the shadow intensity 604 may then be computed from the envelope-detected and speckle reduced frame data 606, O(i,j), using the same expression in Equation 2 with the exception that the input data is speckle reduced, O(i,j), rather than being the original envelope-detected frame data, I(i,j). The bone filter output is then computed by multiplication 608 of the envelope-detected and speckle reduced frame data 606 by the reciprocal of the shadow intensity 604 according to Equation 3, with the exception that the input data is speckle reduced, O(i,j), rather than being the original envelope-detected frame data, I(i,j). Signal separation 610 may then be performed. In one embodiment, the extraction of the bone component 622 may be achieved using a sigmoidal weighting function with the bone filter output from the multiplication 608 step according to Equation 3 as the basis for separation as follows:

$$Y_B(i,j) = 1/(1 + e^{-\gamma_B(B(i,j) - \tau_B)}) \quad (4)$$

where $\gamma_B$ is a parameter of the sigmoidal function that changes the roll-off, $\tau_B$ is the bone separation threshold parameter, and B(i,j) is the bone filter output according to Equation 3, corresponding to the multiplication 608 of the envelope-detected and speckle reduced frame data 606 by the reciprocal of the shadow intensity 604. $Y_B(i,j)$ of Equation 4 represents the bone component 622. The sigmoidal function parameters, $\gamma_B$ and $\tau_B$ may be set as fixed values or may be adaptive to the image data, such as by setting the values to a value proportional to the mean value of the shadow intensity reciprocal 604 or output of the multiplication 608 with the shadow intensity reciprocal 604 and the envelope-detected speckle reduced frame data 606.

Extraction of the tissue component 612 may be achieved in a similar manner using a sigmoidal weighting function with the shadow intensity reciprocal 604 as the basis for separation. A representative tissue extraction equation is as follows:

$$Y_T(i,j) = 1/\left(1 + e^{-\gamma_T\left(\frac{1}{S(i,j)} - \tau_T\right)}\right) \quad (5)$$

where $\gamma_T$ is again a parameter of the sigmoidal function that changes the roll-off, $\tau_T$ is the tissue separation threshold, and 1/S(i,j) is the reciprocal of the shadow intensity 604. The $Y_T$ parameter represents the tissue component 624. The sigmoidal function parameters, $\gamma_T$ and $\tau_T$ may be set as fixed values or may be adaptive to the image data, such as by setting the values to a value proportional to the mean value of the original envelope-detected frame data 602.

After bone and tissue component separation, tissue amplitude mapping 612 and bone amplitude mapping 614 is performed prior to the final summation of the components 618 to form the bone enhanced image 620. The bone amplitude mapping function may take a number of forms but, in some embodiments, may be equal to the bone component $Y_B(i,j)$ 622 from Equation 4. Depending on parameters used in Equation 4, this strategy may result in image regions with positive detection of bone generally exhibiting saturation at the highest image intensity level—in this exemplary embodiment, 1.0.

With the assumption that the bone amplitude mapping function 614 achieves a mean bone image intensity of 1.0, the purpose of the tissue amplitude mapping function 612 is to set the tissue mean and standard deviation such that a user-defined parameter input 616 is achieved in the final bone enhanced image result 620. These user-defined parameters 616 may include, for example, bone-to-tissue contrast and CNR. Contrast, C, and contrast-to-noise, CNR, may be defined as follows:

$$C = 20\log_{10}(\mu_{bone}/\mu_{tissue}) \quad (6)$$

$$CNR = 20\log_{10}\left(\frac{|\mu_{bone} - \mu_{tissue}|}{\sigma_{tissue}}\right) \quad (7)$$

where $\mu_{bone}$, $\mu_{tissue}$, $\sigma_{tissue}$ are the mean and standard deviation of the bone and tissue regions in the image, respectively. Therefore, the goal of the tissue amplitude mapping function is to set the tissue component mean and standard deviation such that Equations. 6 and 7 provide the desired C and CNR of the final bone enhancement image 620. These target metrics may be achieved using the following consecutively performed steps:

Step 1: $M_T(i,j) = I(i,j)Y_T(i,j) - \hat{\mu}_{tissue}$ \quad (7)

Step 2: $M_T(i,j) = \frac{\sigma_{desired}}{\hat{\sigma}_{tissue}} M_T(i,j)$ \quad (8)

Step 3: $M_T(i,j) = M_T(i,j) + \mu_{desired}$ \quad (9)

where I(i,j) is the original envelope-detected imaging data prior to speckle reduction 602, $M_T(i,j)$ is the tissue amplitude mapping 612 output, $\hat{\mu}_{tissue}$ and $\hat{\sigma}_{tissue}$ are the estimated mean and standard deviation of the tissue component 624 of the original image, $Y_T(i,j)$, and $\mu_{desired}$ and $\sigma_{desired}$ are the desired mean and standard deviation of the final reconstructed image in regions representing tissue. Values for $\mu_{desired}$ and $\sigma_{desired}$ may be chosen to provide the desired contrast and CNR.

The final step in the bone enhancement process 600 is to reconstruct the image by summing 618 the tissue amplitude mapping output with the bone amplitude mapping output to form the bone enhanced image 620.

Figure 7:
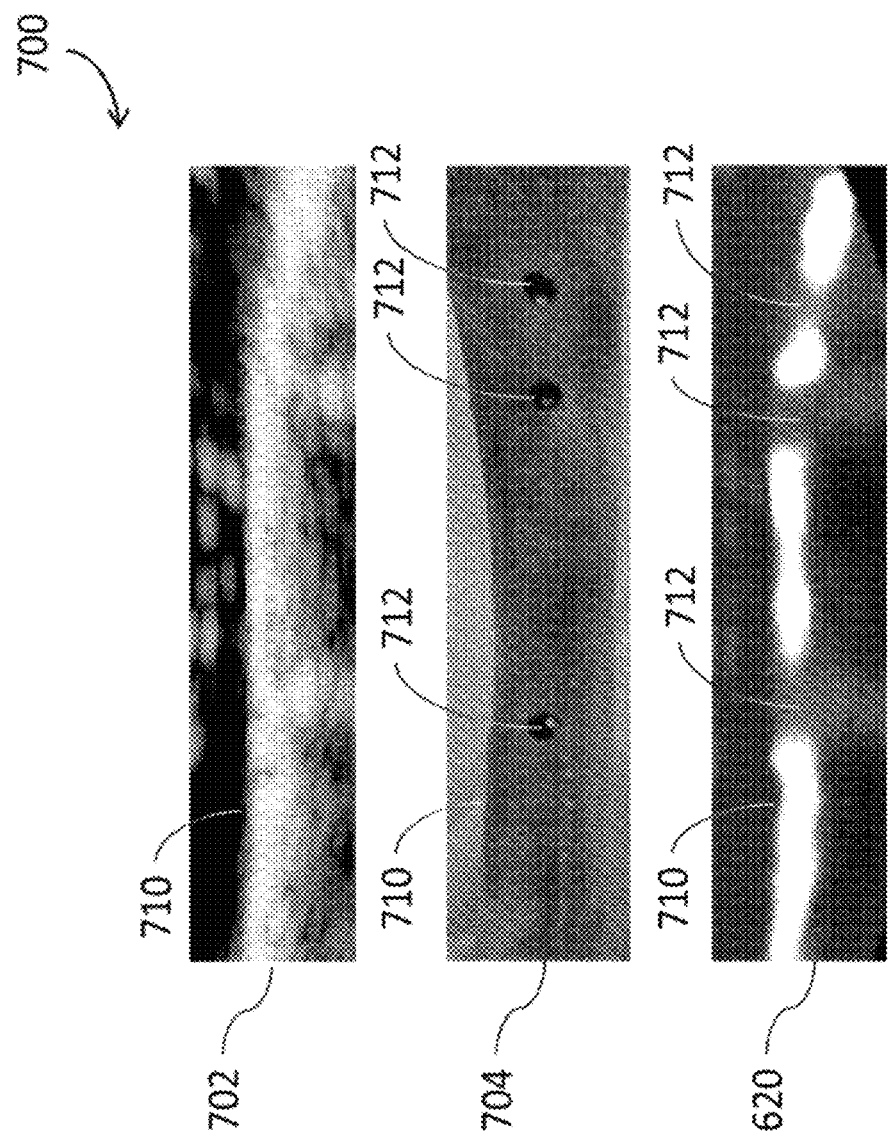
FIG. 7 illustrates the application of the imaging techniques described herein to forming an image of a chicken bone, in accordance with some embodiments of the disclosure provided herein.

FIG. 7 illustrates an exemplary result from a bone enhancement process such as those described in FIGS. 2, 5, and 6. As may be appreciated from the images shown, the bone enhancement process described herein allows for detection of deformations in bone that are less than the original resolution of the ultrasound system. For example, illustrated in FIG. 7 is a photograph of a chicken bone 704 where a small 2.38 mm hole was created that is smaller than the resolution expected from an ultrasound system used to capture ultrasound echo data from the same bone surface. In FIG. 7 a standard ultrasound B-mode 702 of the chicken bone 704 is demonstrated. It may be easily seen from the B-mode image 704 that the holes 712 are not resolvable in the standard B-mode image 710. That is to say that the B-mode image 704 in regions corresponding to the holes 712 do not exhibit a clearly distinct image intensity from that of the surrounding bone surface 710. However, using the bone enhancement technology described herein (e.g. FIG. 6), the holes 712 becomes clearly resolvable. That is to say that the image intensity from the bone enhancement image 620 is clearly distinct from that of the surrounding bone surface 710. It is clear in the bone enhancement image 620 that there is a gap in the bone surface 710 corresponding to a hole 712. This is an unexpected and clinically useful result of the aforementioned bone imaging inventive concepts. Certain prior art has taught methods of bone enhancement that operate after envelope-detected data has been processed to create image data, e.g. B-mode images 702. This image data was then low-pass filtered and then edge detected before quantifying the shadow strength. However, as FIG. 7 illustrates, the B-mode image 702 data formed from the received ultrasound echo data does not enable detection of small deformations in the bone that are less than the resolution of the ultrasound system. In contrast, the current inventors have discovered bone enhancement processes using shadow filter values derived from the envelope-detected form of the received ultrasound echo data or after applying certain speckle reduction processes to the envelope-detected data. These steps enable the bone enhancement image 620 result of FIG. 7 whereby small deformations become easily visible. Detecting features smaller than the resolution of the ultrasound system is useful in clinical applications where localization of small gaps or features in the bone surfaces is desirable. These applications may include, for example, such fracture detection or guidance of injections in or around bone, such as in epidurals or joint injections.

Figure 4:
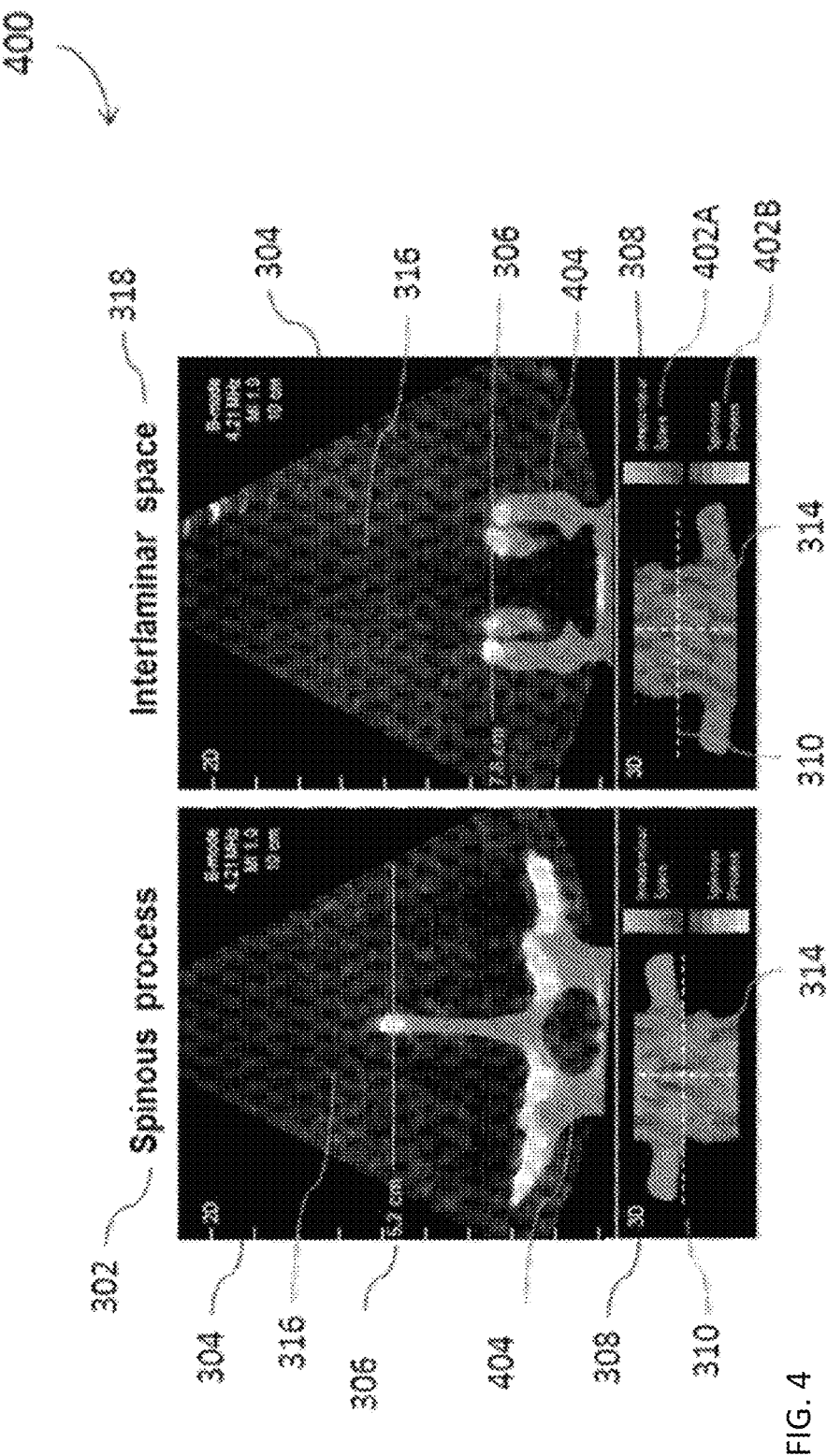
FIG. 4 illustrates a visualization of a 2D ultrasound image overlaid on a corresponding cross-section of a 3D model, in accordance with some embodiments of the disclosure provided herein.

A variety of methods may be employed to create display the simultaneous 2D/3D image display 230. Exemplary embodiments are illustrated in FIGS. 3-4. In some embodiments, the 2D/3D display 230 may contain both a 2D image region 304 and 3D image region 308. A line and or other depth indicator 306 may be overlaid on the 2D image region 304 to indicate the location of a spine landmark, such as a spinous process 302 or interlaminar space 318. In 3D image regions 308, a dashed line or other indicator may be overlaid on the 3D rendering 314 to indicate the location of the current 2D image cross-section 316 relative to the 3D rendering 314. A circle or other indicator 312 overlaid on the 3D image rendering 314 may be displayed to indicate uncertainty in the location of the current 2D image cross-section 316 relative to the 3D rendering 314. In some embodiments, a semi-transparent cross-section 404 of the 3D bone model 224 may be overlaid to the 2D image regions 304. The semi-transparent cross-section 404 derived from the 3D model 224 may have its position and dimensions correspond to the output of the corresponding 3D model registration 222. The amount of transparency may be scaled in proportion to the certainty associated with the corresponding 3D model registration 222. For example, the transparency level may be proportional to a minimized cost function value from the registration process, such as the cost value computed using Equation 1. A lower cost function value would indicate a registration with higher confidence and the cross-section display from the model, in this example, would be less. Furthermore, identification of certain bony landmarks in the 2D image display region 304 may be conveyed using color and/or in any other suitable way (e.g., shading, overlaid indicators, text, etc.). In an exemplary embodiment, the semi-transparent cross-section 404 overlay, the 3D rendering 314, and landmark position indicator 306 may be presented in a blue color if a spinous process landmark is located in the 2D image display 304 during the 3D model registration process 222. Conversely, if the interlaminar space is located in the 2D image display 304 during the 3D model registration process 222, then the semi-transparent cross-section 306 and 3D rendering 314 may be colored orange. In this embodiment, a color map legend 402 in the 3D display region 308 may be included to aid the user in discerning the color-coding for different spinal landmarks detected in the image.

In some embodiments, the display may contain only the 2D image portions of FIGS. 3-4 where the registration process serves to automatically locate landmark depths and/or to provide a 2D cross-section overlay 404. Likewise, only the 3D image portions of FIGS. 3-4 could be shown on the display, in some embodiments. In some embodiments, the 3D image portions may exhibit motion from frame-to-frame, which may be determined from the motion estimates and/or registration output. Alternatively, the cross-section position indicator lines 310 could move relative to the 3D spine, in some embodiments.

Certain inventive aspects relate to the use of the bone enhancement filter to operate on ultrasound imaging data. The following are features that may be used individually or in combination (in combination with each other and/or in combination with other inventive features described elsewhere throughout) in association with certain embodiments. In some embodiments, an offset a may be used that accounts for the bone thickness such that locations in S with lower shadow values correspond to locations in the envelope-detected frame data I with high intensity values of the bone surfaces. In some embodiments, the methods described herein may be applied to the envelope detected ultrasound data, as opposed to a fully processed (envelope detected and log compressed) ultrasound image that has been blurred and then summed with an edge detection version of the blurred image. According to certain embodiments, the reciprocal of the shadow intensity is multiplied by the enveloped detected image intensity. Accordingly, in some embodiments, the shadow intensity values are not self-normalized and subsequently multiplied by the sum of the blurred image with the edge detected output of the blurred image.

Figure 8:
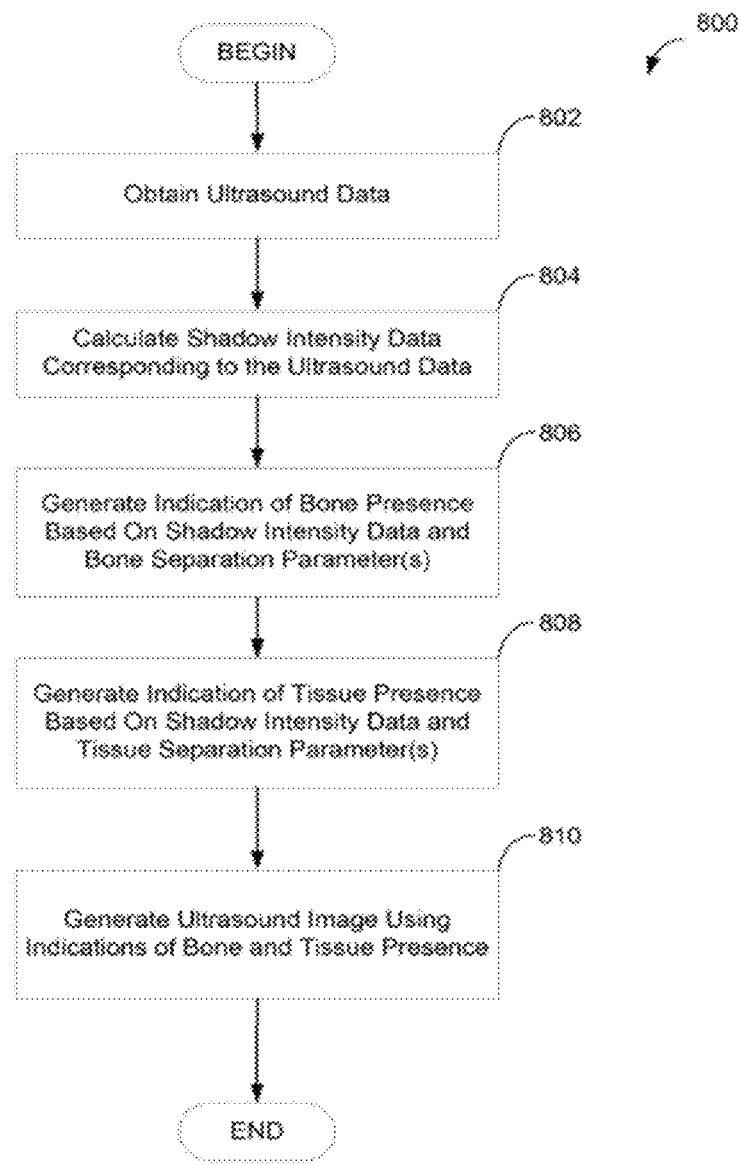
FIG. 8 is a flowchart of an illustrative process of generating an ultrasound image, in accordance with some embodiments of the disclosure provided herein.

Some embodiments of the disclosure provided herein are described below with reference to FIGS. 8 and 9. FIG. 8 is a flowchart of an illustrative process 800 of generating an ultrasound image, in accordance with some embodiments of the disclosure provided herein. Process 800 may be executed by any suitable device and, for example, may be executed by a device comprising one or more ultrasonic transducers (e.g., apparatus 100 described above with reference to FIG. 1), by a device that does not include any ultrasound transducers, by a computer system such as computer system 1000 described below with reference to FIG. 10), multiple computing devices, and/or by any other suitable device or devices.

Process 800 begins at act 802, where ultrasound data is obtained by the device executing process 800. In embodiments where the device executing process 800 comprises one or more ultrasound transducers, the ultrasound data may be obtained from the ultrasound transducer(s) that are part of the device. In other embodiments, regardless of whether the device executing process 800 comprises one or more ultrasound transducers, the ultrasound data may be obtained from another device with which the device executing process 800 is configured to communicate.

Ultrasound data obtained at act 802 may be any suitable type of ultrasound data and, for example, may be ultrasound frame data. In some embodiments, ultrasound data obtained at act 802 may be the ultrasound frame data described with reference to act 202 of FIG. 2. In some embodiments, ultrasound data may comprise a plurality of ultrasound data values each corresponding to a respective voxel in a set of voxels. The value of a voxel may correspond to a value of the subject being imaged at a location in three-dimensional space. As one non-limiting example, the value of a voxel may be a value indicative of an amount of ultrasound energy reflected from the subject at a location in three-dimensional space.

In some embodiments, the obtained ultrasound data may be processed (either before being obtained or after being obtained as part of process 800) using one or more suitable signal processing techniques. For example, in some embodiments, ultrasound data obtained at act 802 may have been demodulated, band pass filtered, and envelope detection may have been applied to the ultrasound data. In some embodiments, one or more of demodulation, band pass filtering, and envelope detection may be applied to the ultrasound data after it is received at act 802.

Next, process 800 proceeds to act 804 where shadow intensity data, corresponding to the ultrasound data obtained at act 802, is calculated. In some embodiments, where the ultrasound data comprises ultrasound data values each corresponding to a voxel in a set of voxels, calculating the shadow intensity data may comprise calculating a shadow intensity value for one or more voxels in the set of voxels. A shadow intensity value for a voxel may be calculated at least in part by calculating a weighted sum of ultrasound data values corresponding to voxels at least a threshold number of voxels away from the first voxel. As one example, a shadow intensity value for a voxel (i,j) may be calculated according to Equation (2) described above, where the constant $\alpha$ is the threshold number of voxels. The threshold number of voxels may be any suitable number (e.g., 0, 1, 2, 3, 5, 10, etc.) of voxels and may be set manually or automatically. In some embodiments, the threshold number of voxels may be set such that the voxels whose values are used to calculate the shadow intensity value do not correspond to locations in or on the surface of a bone. In some embodiments, the threshold number of voxels may be greater than or equal to an axial resolution of the imaging system used to generate the ultrasound data. It should be appreciated that shadow intensity data may be obtained in any other suitable way, as aspects of the disclosure provided herein are not limited in this respect.

After shadow intensity data is calculated at act 804, process 800 proceeds to act 806, where an indication of bone presence in an imaged region of a subject is generated. The indication of bone presence may provide an indication, for each of one or more voxels in the imaged region of a subject, whether bone is present at the location in the subject to which the voxel corresponds. Calculating an indication of bone presence at a particular voxel may comprise calculating a bone intensity value, which may indicate a likelihood of bone presence such that higher (or, in another embodiment, lower) values indicate an increased likelihood of bone presence and lower (or, in another embodiment, higher) values indicate a decreased likelihood of bone presence. In some embodiments, a bone intensity value for a voxel may be calculated based at least in part on a ratio of an ultrasound data value corresponding to the voxel (obtained at act 802) and a shadow intensity value corresponding to the voxel (obtained at act 804). The bone intensity value may be obtained at least in part by applying a function (e.g., a sigmoidal weighting function) to the ratio of the ultrasound data value corresponding to the voxel and the shadow intensity value corresponding to the voxel. The function may depend on one or more bone separation parameters, each of which may be set as fixed values or may be calculated based at least in part on ultrasound data (obtained at act 802) and/or shadow intensity data (obtained at act 804).

As one non-limiting example, the indication of bone presence may be calculated according to Equation (4) described above. In particular, Equation (4) may be used to calculate one or more bone intensity values using a function parameterized by two bone separation parameters $\gamma_B$ and $\tau_B$. One or both of these parameters may be calculated based, at least in part, on the shadow intensity data, as described above with reference to Equation (4). It should be appreciated, however, that Equation (4) is an illustrative non-limiting example of how to calculate bone intensity values and that bone intensity values may be calculated in any other suitable way.

Next, process 800 proceeds to act 808, where an indication of tissue presence in an imaged region of a subject is generated. The indication of tissue presence may provide an indication, for each of one or more voxels in the imaged region of a subject, whether tissue is present at the location in the subject to which the voxel corresponds. Calculating an indication of tissue presence at a particular voxel may comprise calculating a tissue intensity value, which may indicate a likelihood of tissue presence such that higher (or, in another embodiment, lower) values indicate an increased likelihood of tissue presence and lower (or, in another embodiment, higher) values indicate a decreased likelihood of tissue presence. In some embodiments, a tissue intensity value for a voxel may be calculated based at least in part the shadow intensity value corresponding to the voxel. The tissue intensity value may be calculated by evaluating a function (e.g., a sigmoidal weighting function) at least in part by using the shadow intensity value corresponding to the voxel. The function may depend on one or more tissue separation parameters, each of which may be set as fixed values or may be calculated based at least in part on ultrasound data (obtained at act 802) and/or shadow intensity data (obtained at act 804).

As one non-limiting example, the indication of tissue presence may be calculated according to Equation (5) described above. In particular, Equation (5) may be used to calculate one or more tissue intensity values using a function parameterized by two tissue separation parameters $\gamma_T$ and $\tau_T$. One or both of these parameters may be calculated based, at least in part, on the ultrasound data obtained at act 802 (e.g., based on envelope-detected frame data, as described above with reference to Equation (5)). It should be appreciated that Equation (5) is an illustrative non-limiting example of how to calculate tissue intensity values and that tissue intensity values may be calculated in any other suitable way.

In some embodiments, indications of bone and tissue presence may be calculated using one or more bone separation parameters different from one or more tissue separation parameters. As one example, the parameters $\gamma_B$ and $\gamma_T$ in Equations (4) and (5) may have different values. Additionally, or alternatively, the parameters $\tau_B$ and $\tau_T$ in Equations (4) and (5) may have different values. As may be appreciated from the foregoing, in some embodiments, the indications of bone and tissue presence may be calculated independently from one another rather than being derived from one another. That is, in some embodiments, the indication of tissue presence is not derived from the indication of bone presence (e.g., by calculating a tissue intensity value for a voxel as 1 minus bone intensity value for the voxel), but is computed directly from the shadow intensity data.

Next, process 800 proceeds to act 810, where an ultrasound image is generated, at least in part, by using the indications of bone presence and tissue presence obtained at act 806 and 808, respectively. This may be done in any suitable way. In some embodiments, the indications of bone and tissue presence may be combined to form an ultrasound image having a desired bone-to-tissue contrast and/or a desired contrast-to-noise ratio. This may be done as described above with reference to Equations (6)-(9) or in any other suitable way. After act 810 is executed, process 800 completes.

Figure 9:
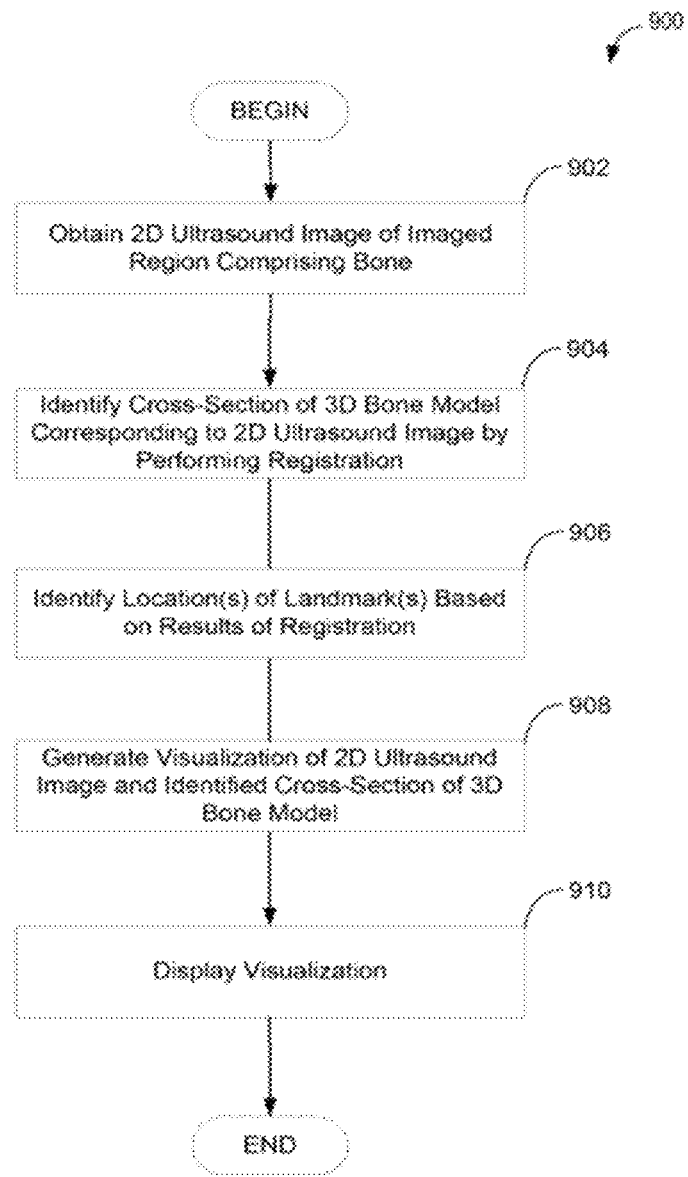
FIG. 9 is a flowchart of an illustrative process of generating a visualization of a 2D ultrasound image and corresponding cross-section of a 3D bone model, in accordance with some embodiments of the disclosure provided herein.

FIG. 9 is a flowchart of illustrative process 900 of generating a visualization of a 2D ultrasound image and a corresponding cross-section of a 3D bone model, in accordance with some embodiments of the disclosure provided herein. Process 900 may be executed by any suitable device and, for example, may be executed by a device comprising one or more ultrasonic transducers (e.g., apparatus 100 described above with reference to FIG. 1), by a device that does not include any ultrasound transducers, by a computer system such as computer system 1000 described below with reference to FIG. 10), multiple computing devices, and/or by any other suitable device or devices.

Process 900 begins at act 902, where a two-dimensional (2D) ultrasound image of an imaged region of a subject is obtained. The imaged region may comprise bone. For example, the imaged region may comprise at least a portion of the spine (e.g., lumbar spine) of a subject being imaged and/or any other suitable bone of a subject, as aspects of the disclosure provided herein are not limited to imaging of any particular bone(s) of the subject and may be applied to imaging any bone(s) of the subject. The two-dimensional ultrasound image may be obtained using any of the techniques described herein (e.g., process 800) or in any other suitable way.

Next, process 900 proceeds to act 904 where a portion of a three-dimensional (3D) model of the bone corresponding to the 2D ultrasound image is identified. In some embodiments, the 3D bone model comprises two or more 2D cross sections and act 904 comprises identifying a 2D cross section of the 3D model corresponding to the ultrasound image obtained at act 902. As described above, in some embodiments, a 2D cross section of a 3D bone model may comprise one or more "model template" vectors each of which may represent one or more anatomical landmarks (e.g., one or more vertebral landmarks, one or more spinous processes, one or more interlaminar spaces, etc.).

In some embodiments, the portion of a 3D model of the bone corresponding to the 2D ultrasound image may be identified by using a registration technique. Any of the above-described registration techniques or any other suitable registration technique(s) may be used to identify the portion of the 3D model of the bone corresponding to the 2D ultrasound image, as aspects of the disclosure provided herein are not limited in this respect. In some embodiments, the registration may be performed at least in part by using information about motion of the subject during generation of the 2D ultrasound image. In this way, any motion by the subject during imaging may be taken into account when identifying a cross-section of the 3D model of the bone that corresponds to the image of the subject obtained while the subject was moving.

Next, process 900 proceeds to act 906, where the location(s) of one or more anatomical landmarks of the subject are identified in the 2D ultrasound image based on results of the registration. It should be appreciated that, unlike some conventional approaches to performing registration by first identifying anatomical landmarks and performing registration based on the identified anatomical landmarks, the anatomical landmarks are not used to perform the registration in process 900, in some embodiments. Rather, anatomical landmarks may be identified based on results of the registration process at act 906 of process 900, and this may be done in any suitable way. As one illustrative example, the 3D model of the bone may indicate one or more anatomical landmarks and the results of the registration may be used to identify corresponding anatomical landmarks in the 2D ultrasound image.

Next, process 900 proceeds to act 908, where a visualization of the 2D ultrasound image and identified cross-section of the 3D model is generated. The visualization may indicate the location of one or more anatomical landmarks identified at act 906. For example, in the application of imaging a lumbar spine, the visualization may indicate the location of the spinous process and/or an interlaminar space.

In some embodiments, generating the visualization may comprise overlaying the identified 2D cross section on the 2D ultrasound image (see e.g., FIG. 4). Performing the overlaying may comprise performing an affine transformation of the identified 2D cross section so that the cross-section and the ultrasound image line up when displayed. In some embodiments, generating the visualization may comprise generating the visualization to include at least a portion of the 3D model of the bone and information identifying how the 2D ultrasound image correspond to the 3D model of the bone, as illustrated in FIG. 4, for example.

In some embodiments, the identified 2D cross section is overlaid on the 2D ultrasound image with a degree of transparency that is determined based, at least in part, on results of the registration. The degree of transparency may be determined using a measure of quality of fit between the 2D ultrasound image and the identified cross section. Any suitable measure of fit may be used (e.g., a measure of uncertainty associated with the registration, Equation (1), a goodness-of-fit metric, Euclidean distance, etc.), as aspects of the disclosure provided herein are not limited in this respect. In some embodiments, the degree of transparency may be inversely proportional to the goodness of fit. For example, the better the fit between the 2D ultrasound image and the identified 2D cross section of the 3D bone model, the less transparency may be used to overlay the identified 2D cross section on the ultrasound image. Similarly, the worse the fit between the 2D ultrasound image and the identified 2D cross section of the 3D bone model, the more transparency may be used to overlay the identified 2D cross-section on the ultrasound image. In this way, transparency may be used to reduce impact of poor registration results on the user.

Next, process 900 proceeds to act 910, where the visualization generated at act 908 is displayed. The visualization may be displayed using the device executing process 900 (e.g., device 100 described with reference to FIG. 1) or any other suitable device(s) (e.g., one or more displays), as aspects of the disclosure provided herein are not limited in this respect. After act 910 is performed, process 900 completes.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media may be transportable, such that the program or programs stored thereon may be loaded onto one or more different computers or other processors to implement various ones of the aspects described above. In some embodiments, computer readable media may be non-transitory media.

Figure 10:
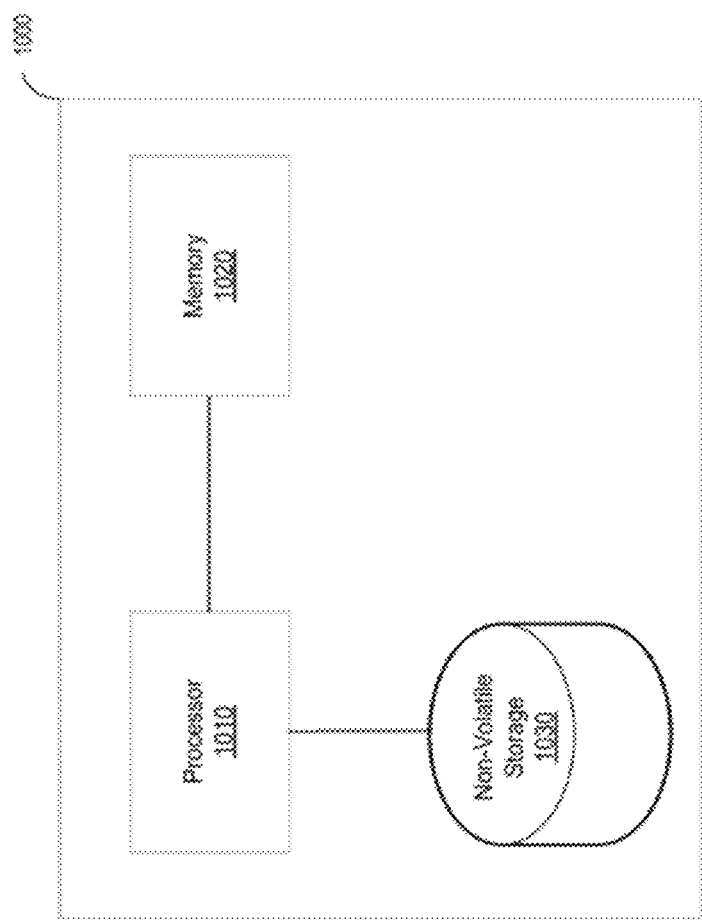
FIG. 10 is a block diagram of an illustrative computer system on which embodiments described herein may be implemented.

An illustrative implementation of a computer system 1000 that may be used in connection with any of the embodiments of the disclosure provided herein is shown in FIG. 10. The computer system 1000 may include one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the disclosure provided herein are not limited in this respect. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A processor-based method for visualizing ultrasound data, the method comprising:
    obtaining ultrasound data, including image intensity values, that represents a two-dimensional (2D) ultrasound image of an imaged region of a subject, the imaged region comprising bone, the ultrasound data including pixel locations having respective pixel depths;
    applying a bone filter to the ultrasound data to determine possible bone surface locations;
    providing a three-dimensional (3D) simulated model of a human bone having a size and shape representative of a human population, wherein the 3D simulated model is defined prior to obtaining the 2D ultrasound image of such subject;
    identifying model template cross-sections of the (3D) simulated model of the human bone corresponding to the 2D ultrasound image comprising registering the possible bone surface locations in the 2D ultrasound image to the 3D simulated model,
    identifying at least one location of at least one landmark feature of the bone in the 2D ultrasound image based on results of the registration; and
    generating a visualization that includes: (a) a visualization of the 2D ultrasound image that comprises the bone and (b) a visualization of one of the identified cross-sections of the 3D simulated model of the human bone that were defined prior to obtaining the 2D ultrasound image and identified at least in part by registering the 2D ultrasound image to the 3D simulated model, wherein the visualization indicates the at least one location of the at least one landmark feature.

2. The processor-based method of claim 1, wherein in the visualization that includes: (a) the visualization of the 2D ultrasound image that comprises the bone and (b) the visualization of one of the identified cross-sections of the 3D simulated model of the human bone that was defined prior to obtaining the 2D ultrasound image and identified at least in part by registering the 2D ultrasound image to the simulated 3D model, the visualization of the 2D ultrasound image that comprises the bone does not overlap the visualization of the one of the identified cross-sections of the 3D simulated model of the human bone that were defined prior to obtaining the 2D ultrasound image and identified at least in part by registering the 2D ultrasound image to the 3D simulated model.

3. The processor-based method of claim 1, wherein in the visualization that includes: (a) the visualization of the 2D ultrasound image that comprises the bone and (b) the visualization of one of the identified cross-sections of the 3D simulated model of the human bone that was defined prior to obtaining the 2D ultrasound image and identified at least in part by registering the 2D ultrasound image to the 3D simulated model, the visualization of the 2D ultrasound image that comprises the bone is spaced apart from the visualization of the one of the identified cross-sections of the 3D simulated model of the human bone that were defined prior to obtaining the 2D ultrasound image and identified at least in part by registering the 2D ultrasound image to the 3D simulated model.

4. The processor-based method of claim 1, wherein:
    the possible bone surface locations comprise a first set of points extracted from the bone-filtered ultrasound data, and
    registering the possible bone surface locations in the 2D ultrasound image to the 3D simulated model comprises comparing the first set of points with a second set of points extracted from the 3D simulated model of the human bone.

5. The processor-based method of claim 4, wherein comparing the first set of points with the second set of points comprises identifying a translation and/or scaling of the first or second set of points that minimizes a cost function.

6. The processor-based method of claim 1, wherein registering the possible bone surface locations in the 2D ultrasound image to the 3D simulated model comprises determining a maximum image intensity summed along intersections of the 3D simulated model and the 2D ultrasound image.

7. The processor-based method of claim 6, wherein determining the maximum image intensity comprises varying a translation and a scaling of the 2D ultrasound image relative to the 3D simulated model.

8. The processor-based method of claim 1, wherein registering the possible bone surface locations in the 2D ultrasound image to the 3D simulated model comprises using a coarse-to-fine registration technique.

9. At least one non-transitory computer readable storage medium storing processor-executable instructions that, when executed by at least one processor, result in a method comprising:
  obtaining ultrasound data, including image intensity values, that represent a two-dimensional (2D) ultrasound image of an imaged region of a subject, the imaged region comprising bone, the ultrasound data including pixel locations having respective pixel depths;
  applying a bone filter to the ultrasound data to determine possible bone surface locations;
  identifying model template cross-sections of a three-dimensional (3D) simulated model of the bone corresponding to the 2D ultrasound image at least in part by registering the possible bone surface locations in the 2D ultrasound image to the 3D simulated model, wherein the model template cross-sections are defined prior to obtaining such 2D ultrasound image of such subject, the model template cross-sections having a size and shape representative of a population of potential subjects;
  identifying at least one location of at least one landmark feature of the bone in the 2D ultrasound image based on results of the registration; and
  generating a visualization that includes: (a) a visualization of the 2D ultrasound image that comprises the bone and (b) a visualization of one of the identified cross-sections of the 3D simulated model of the bone that was defined prior to obtaining the 2D ultrasound image and identified at least in part by registering the 2D ultrasound image to 3D simulated model, wherein the visualization indicates the at least one location of the at least one landmark feature.

10. The at least one non-transitory computer readable storage medium of claim 9, wherein in the visualization that includes: (a) the visualization of the 2D ultrasound image that comprises the bone and (b) the visualization of one of the identified cross-sections of the 3D simulated model of the bone that was defined prior to obtaining the 2D ultrasound image and identified at least in part by registering the 2D ultrasound image to the 3D simulated model, the visualization of the 2D ultrasound image that comprises the bone does not overlap the visualization of the one of the identified cross-sections of the 3D simulated model of the bone that were defined prior to obtaining the 2D ultrasound image and identified at least in part by registering the 2D ultrasound image to the 3D simulated model.

11. The at least one non-transitory computer readable storage medium of claim 9, wherein in the visualization that includes: (a) the visualization of the 2D ultrasound image that comprises the bone and (b) the visualization of one of the identified cross-sections of the 3D simulated model of the bone that was defined prior to obtaining the 2D ultrasound image and identified at least in part by registering the 2D ultrasound image to the 3D simulated model, the visualization of the 2D ultrasound image that comprises the bone is spaced apart from the visualization of the one of the identified cross-sections of the 3D simulated model of the bone that were defined prior to obtaining the 2D ultrasound image and identified at least in part by registering the 2D ultrasound image to the 3D simulated model.

12. A system for processing ultrasound data, the system comprising:
  at least one computer hardware processor;
  at least one ultrasound imaging unit coupled to said processor;
  said processor including circuitry that obtains ultrasound data, including image intensity values, that represent a two-dimensional (2D) ultrasound image of an imaged region of a subject, the imaged region comprising bone, the ultrasound data including pixel locations having respective pixel depths;
  said processor including circuitry that applies a bone filter to the ultrasound data to determine possible bone surface locations;
  said processor including circuitry that identifies model template cross-sections of a three-dimensional (3D) simulated model of the bone corresponding to the 2D ultrasound image at least in part by registering the possible bone surface locations in the 2D ultrasound image to the 3D simulated model, wherein the model template cross-sections are defined prior to obtaining such 2D ultrasound image of such subject, the model template cross-sections having a size and shape representative of a population of potential subjects;
  said processor including circuitry that identifies at least one location of at least one landmark feature of the bone in the 2D ultrasound image based on results of the registration; and
  said processor including circuitry that generates a visualization that includes: (a) a visualization of the 2D ultrasound image that comprises the bone and (b) a visualization of one of the identified cross-sections of the 3D simulated model of the bone that were defined prior to obtaining the 2D ultrasound image and identified at least in part by registering the 2D ultrasound image to the 3D simulated model, wherein the visualization indicates the at least one location of the at least one landmark feature.

13. The system of claim 12, wherein in the visualization that includes:
  (a) the visualization of the 2D ultrasound image that comprises the bone and (b) the visualization of one of the identified cross-sections of the 3D simulated model of the bone that was defined prior to obtaining the 2D ultrasound image and identified at least in part by registering the 2D ultrasound image to the 3D simulated model, the visualization of the 2D ultrasound image that comprises the bone does not overlap the visualization of the one of the identified cross-sections of the 3D simulated model of the bone that were defined prior to obtaining the 2D ultrasound image and identified at least in part by registering the 2D ultrasound image to the 3D simulated model.

14. The system of claim 12, wherein in the visualization that includes:
  (a) the visualization of the 2D ultrasound image that comprises the bone and (b) the visualization of one of the identified cross-sections of the 3D simulated model of the bone that was defined prior to obtaining the 2D ultrasound image and identified at least in part by registering the 2D ultrasound image to the simulated model, the visualization of the 2D ultrasound image that comprises the bone is spaced apart from the visualization of the one of the identified cross-sections of the 3D simulated model of the bone that were defined prior to obtaining the 2D ultrasound image and identified at least in part by registering the 2D ultrasound image to the 3D simulated model.

* * * * *